(12) United States Patent
Suzuki

(10) Patent No.: US 8,308,766 B2
(45) Date of Patent: *Nov. 13, 2012

(54) ENDOSCOPIC TREATMENT INSTRUMENT

(75) Inventor: Takayuki Suzuki, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 642 days.

This patent is subject to a terminal disclaimer.

(21) Appl. No.: 11/711,540

(22) Filed: Feb. 27, 2007

(65) Prior Publication Data

US 2008/0208219 A1 Aug. 28, 2008

(51) Int. Cl.
*A61B 17/04* (2006.01)
(52) U.S. Cl. .......... 606/232; 606/139; 606/144
(58) Field of Classification Search .......... 606/232, 606/144, 148, 145, 139, 142, 143, 200, 213; 623/1.11; 600/7
See application file for complete search history.

(56) References Cited

U.S. PATENT DOCUMENTS

| | | | |
|---|---|---|---|
| 5,507,754 A | | 4/1996 | Green et al. |
| 5,562,689 A | * | 10/1996 | Green et al. ............ 606/151 |
| 5,624,396 A | | 4/1997 | McNamara et al. |
| 5,674,231 A | * | 10/1997 | Green et al. ............ 606/142 |
| 2002/0065524 A1 | * | 5/2002 | Miller et al. ............ 606/139 |
| 2003/0236535 A1 | | 12/2003 | Onuki et al. |
| 2004/0249395 A1 | * | 12/2004 | Mikkaichi et al. ....... 606/144 |
| 2005/0251205 A1 | | 11/2005 | Ewers et al. |
| 2005/0261710 A1 | | 11/2005 | Sakamoto et al. |
| 2007/0073320 A1 | | 3/2007 | Mikkaichi et al. |

FOREIGN PATENT DOCUMENTS

| | | |
|---|---|---|
| EP | 1484023 A1 | 12/2004 |
| JP | S54-166093 U | 11/1979 |
| JP | 2001-46514 A | 2/2001 |
| JP | 2004-601 A | 1/2004 |
| WO | WO 2005/110244 A1 | 11/2005 |

OTHER PUBLICATIONS

European Search Report dated Dec. 4, 2008 from corresponding European Patent Application No. EP 08 00 3366.5.
Japanese Office Action dated Jul. 31, 2012 from corresponding Japanese Patent Application No. 2008-014121, together with an English language translation.

* cited by examiner

*Primary Examiner* — Julian Woo
*Assistant Examiner* — Christopher L Templeton
(74) *Attorney, Agent, or Firm* — Scully, Scott, Murphy & Presser, PC

(57) ABSTRACT

An endoscopic treatment instrument is provided which includes: a flexible sheath; a wire disposed inside the sheath so as to advance and retreat; a restriction member which restricts a movement of the wire in the sheath to a proximal side; an operating portion connected to a proximal end of the sheath; a wire operating portion which is connected to a proximal end of the wire and disposed to advance and retreat relative to the operating portion; a resilient member which has a first end and a second end and of which the first end is connected to the wire operating portion to expand and contract between the second end; a movable member which is connected to the second end so as to be movable relative to the operating portion; and a control member which is disposed in the movable member and which switches the movable member between a movable state and a fixed state relative to the operating portion.

3 Claims, 42 Drawing Sheets

ENDOSCOPIC TREATMENT INSTRUMENT

BACKGROUND OF THE INVENTION

1. Field of the Invention

The present invention relates to an endoscopic treatment instrument using an endoscope.

2. Description of the Related Art

When a treatment is performed inside a human body, it can be classified into surgical incision of the patient's body and oral or anal endoscopic treatment. The oral endoscopic treatment can be used to suture a perforation of a digestive canal. At this time, a suture tool having a suture thread extending from an anchor is inserted to a perforation in an oral endoscopic manner, punctures a tissue in the vicinity of the perforation with the suture tool housed in a puncture needle, and pushes up the anchor connected to the suture thread out of the puncture needle. By pulling out the puncture needle from the tissue and then tying two suture threads with the perforation interposed therebetween, the perforation is sutured (see U.S. patent application Ser. No. 11/238,016).

SUMMARY OF THE INVENTION

An aspect of the invention includes: a flexible sheath; a wire disposed inside the sheath so as to advance and retreat; a restriction member which restricts movement of the wire in the sheath to a proximal side; an operating portion connected to a proximal end of the sheath; a wire operating portion which is connected to a proximal end of the wire and disposed to advance and retreat relative to the operating portion; a resilient member which has a first end and a second end and of which the first end is connected to the wire operating portion to expand and contract between the second end; a movable member which is connected to the second end so as to be movable relative to the operating portion; and a control member which is disposed in the movable member and which switches the movable member between a movable state and a fixed state relative to the operating portion.

BEST MODE FOR CARRYING OUT THE INVENTION

Figure 1:
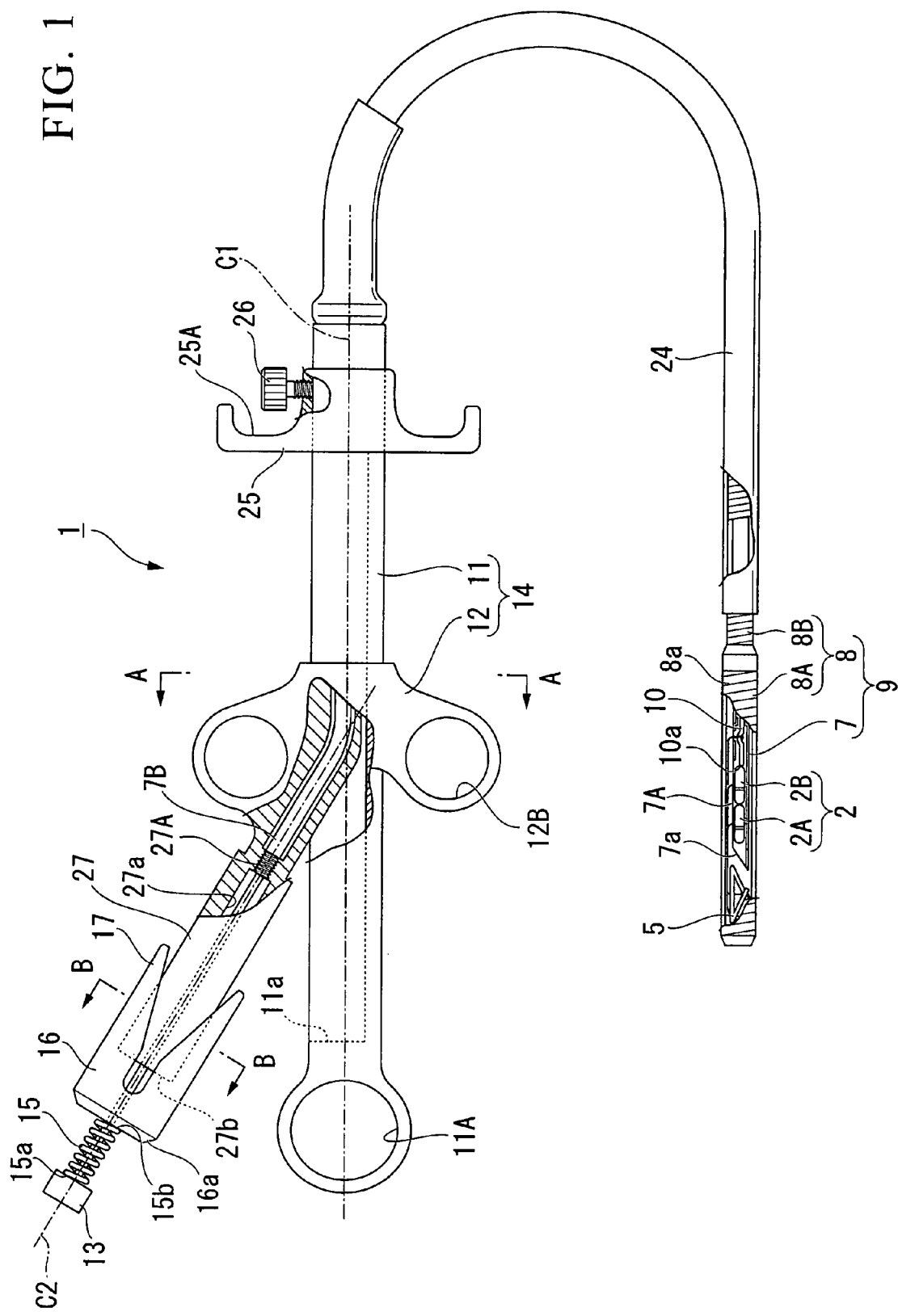
FIG. 1 is a diagram illustrating the entire general appearance of a suture instrument according to a first embodiment of the invention.

Best mode for carrying out the invention will be described in detail below. In the following description, like elements are denoted by like reference numerals and repeated description is omitted.

First Embodiment

Figure 2:
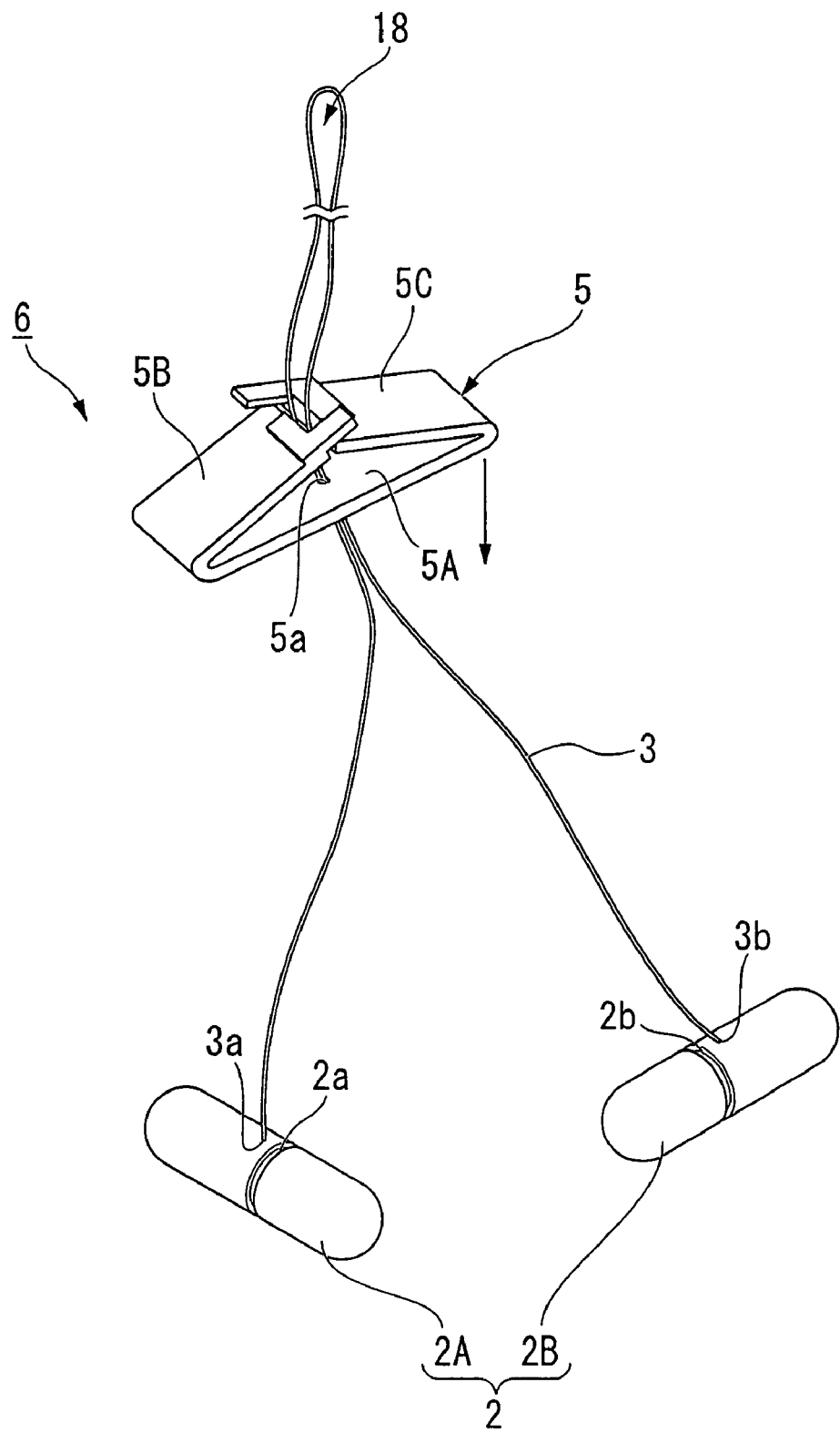
FIG. 2 is a diagram illustrating the entire general appearance of a suture tool used in the suture instrument according to the first embodiment of the invention.
Figure 3:
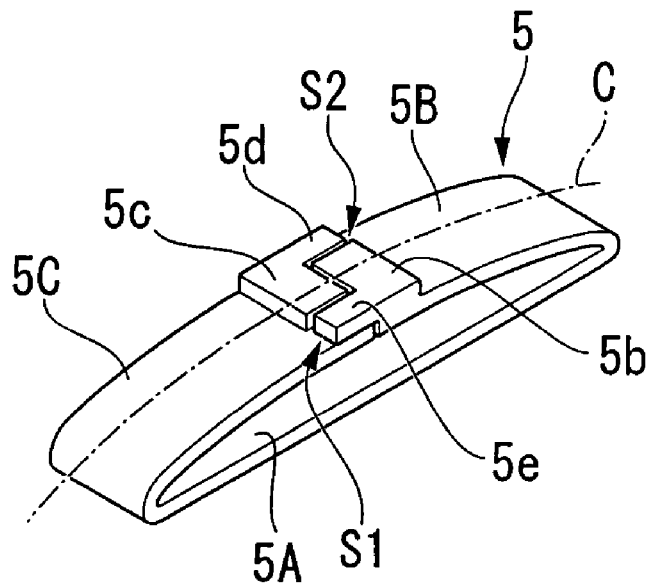
FIG. 3 is a perspective view illustrating a stopper of the suture tool.
Figure 4:
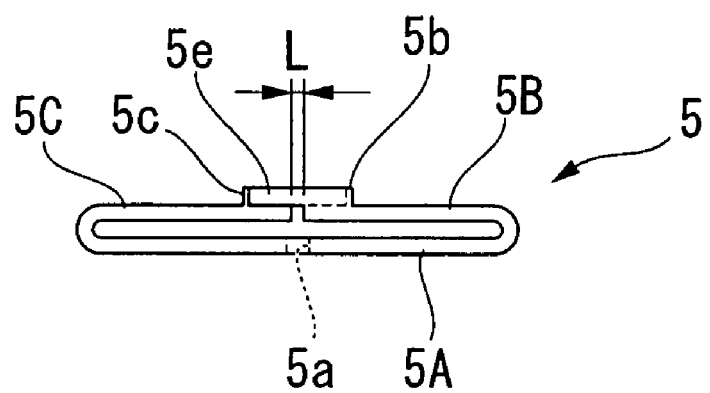
FIG. 4 is a side view of the stopper shown in FIG. 3.
Figure 5:
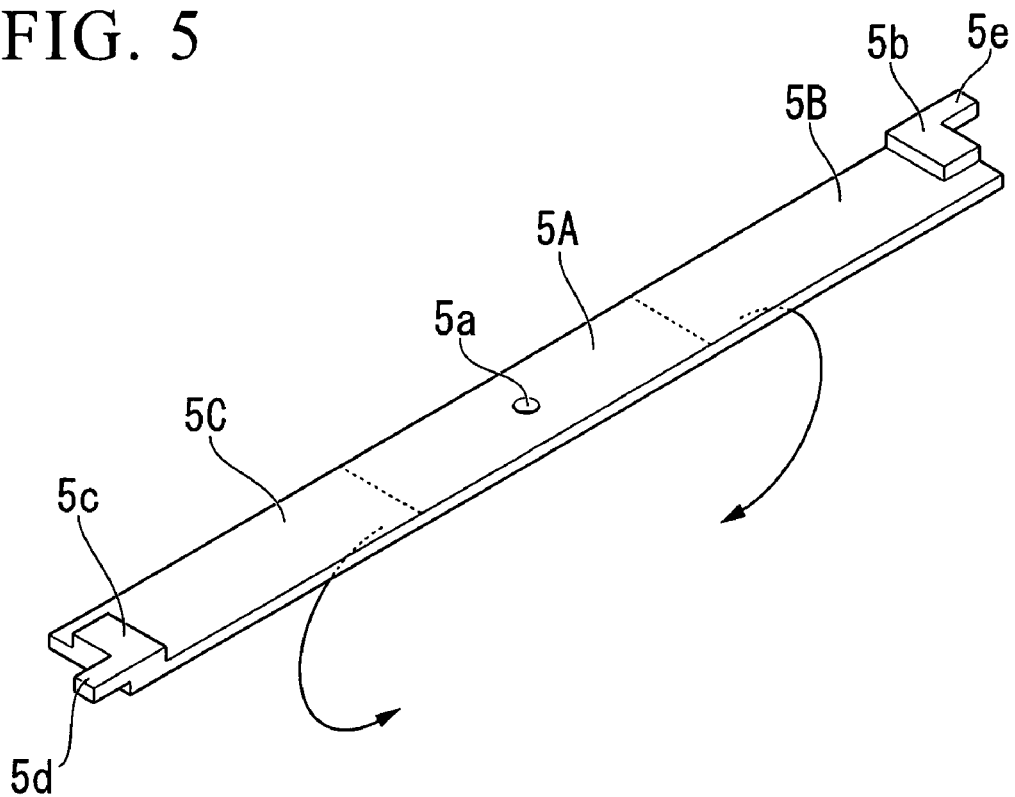
FIG. 5 is a development view illustrating the stopper shown in FIG. 3.

As shown in FIGS. 1 and 2, a suture instrument (endoscopic treatment instrument) 1 according to a first embodiment of the present invention includes a suture tool 6 having an anchor 2 anchored to a biological tissue which is not shown, a suture thread 3 drawn out of the anchor 2, and a stopper 5 disposed on the suture thread 3; a sheath 9 having a hollow puncture needle 7, which can house the anchor 2 thereinside, having a hard needle portion 7A formed with an opening 7a at the distal end thereof and an outer sheath 8 which houses the puncture needle 7 so as to advance and retreat; an operating portion 14 having a pusher (wire) 10 which is disposed to advance and retreat in the puncture needle 7 and a proximal side of which extends to a proximal side with its distal end 10a being in contact with the anchor 2, an operating portion body 11 which is connected to and extends from a proximal end of the outer sheath 8, and a needle slider (a first operating portion) 12 which is firmly fixed to a proximal end of the puncture needle 7 and disposed to the operating portion body 11 so as to advance and retreat; a pusher operating portion (a wire operating portion, a second operating portion) 13 which is connected to a proximal end of the pusher 10 and disposed to the operating portion body 11 so as to advance and retreat; a spring member (a resilient member) 15 which has a first end 15a and a second end 15b and the first end 15a is connected to the pusher operating portion 13 and which expands and contracts between the second end 15b; a movable stopper (movable member) 16 which is connected to the second end 15b and which is movable relative to the operating portion 12; and a lock member (a control member) 17 which is disposed in the movable stopper 16 and which switches the movable stopper 16 between a movable state and a fixed state relative to the operating section 12.

The anchor 2 of the suture tool 6 includes a first anchor 2A and a second anchor 2B. The anchors 2A and 2B have the same elongated cylindrical shape and have a groove 2a in the circumferential direction at the center portion thereof. A first end 3a of the suture thread 3 is connected to and extended from the vicinity of the groove 2a of the first anchor 2A and is bent back to form a loop 18 in which the pusher 10 is able to be inserted, and a second end 3b is connected to the vicinity of the groove 2b of the second anchor 2B.

As shown in FIGS. 3 to 6, the stopper 5 has a base portion 5A and a pair of bent pieces 5B and 5C which are formed by bending back both end sides of a band-shaped thin plate member toward the center side. The base portion 5A of the stopper 5 is provided with a through-hole 5a through which the suture thread 3 can be inserted. The pair of bent pieces 5B and 5C is disposed to be substantially parallel to the base portion 5A.

The distal ends of the pair of bent pieces 5B and 5C are provided with thick plate portions 5b and 5c, which are thick in the insertion direction of the suture thread 3 and sandwich the suture thread 3 therebetween, at positions decentered in a direction separating each other from the center axis C of the pair of bent pieces 5B and 5C. The distance L between the thick plate portions 5b and 5c is smaller than the diameter of the suture thread 3.

An engaging protrusion portion 5d protruding toward a gap S1 formed between a side periphery of the bent piece 5B and the thick plate portion 5b due to the decenterization is formed in the thick plate portion 5c disposed in the other bent piece 5C which is opposing the bent piece 5B. Similarly, an engaging protrusion portion 5e protruding toward a gap S2 formed between a side periphery of the bent piece 5C and the thick plate portion 5c is formed in the thick plate portion 5b disposed in the bent piece 5B.

Figure 6:
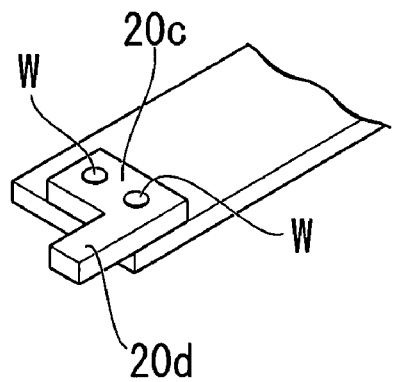
FIG. 6 is a partially enlarged view illustrating a modified example of the stopper shown in FIG. 3.

The stopper 5 is shaped by pressing portions other than the thick plate portions 5b and 5c of the band-shaped thin plate member with a thickness of 0.4 mm to 0.2 mm. Thereafter, portions which are away from both ends by predetermined length are bent back toward the center to form the base portion 5A and the pair of bent pieces 5B and 5C. Alternatively, as shown in FIG. 6, a thick plate portion 20c and an engaging protrusion portion 20d, a thickness of which being 0.4 mm, may be secured to both ends of a band-shaped thin plate member with a thickness of 0.2 mm by means of caulking or welding W to form a stopper 20.

The puncture needle 7 is further provided with a tube-shaped proximal member 7B in which the needle portion 7A is connected to the distal end thereof. The proximal member 7B is formed of a flexible soft member. The proximal member 7B is formed of an extrusion-molded tube of PEEK (Poly Ether Ether Ketone) so as to endure, for example, an expanding and contracting load, which is to be described later, accompanied with the protruding and retracting of the puncture needle 7 relative to the outer sheath 8 and an expanding load due to the movement of the stopper 5 over the suture thread 3 accompanied with a tightening of biological tissue.

Figure 7:
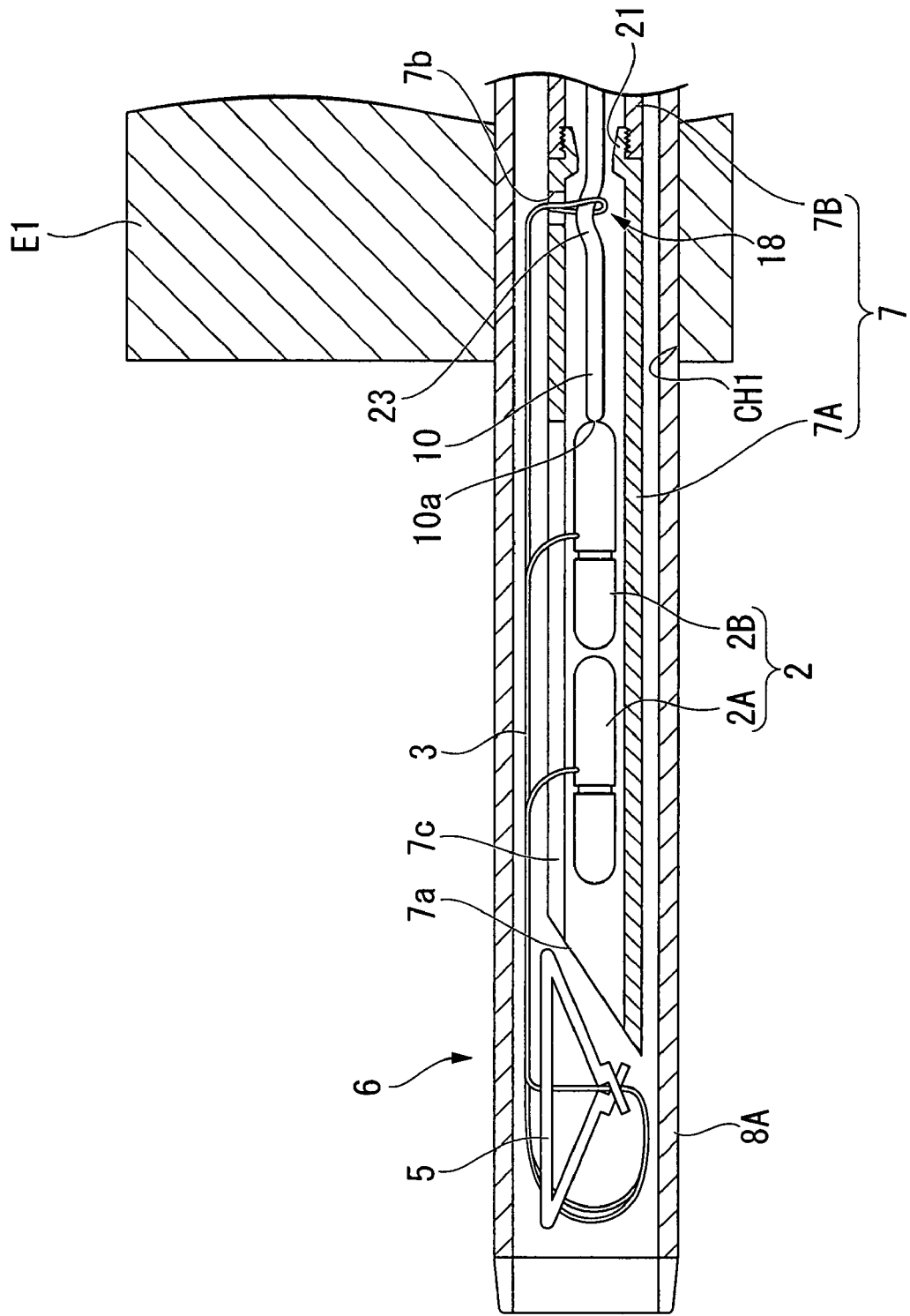
FIG. 7 is a partially enlarged sectional view of the suture instrument.
Figure 8:
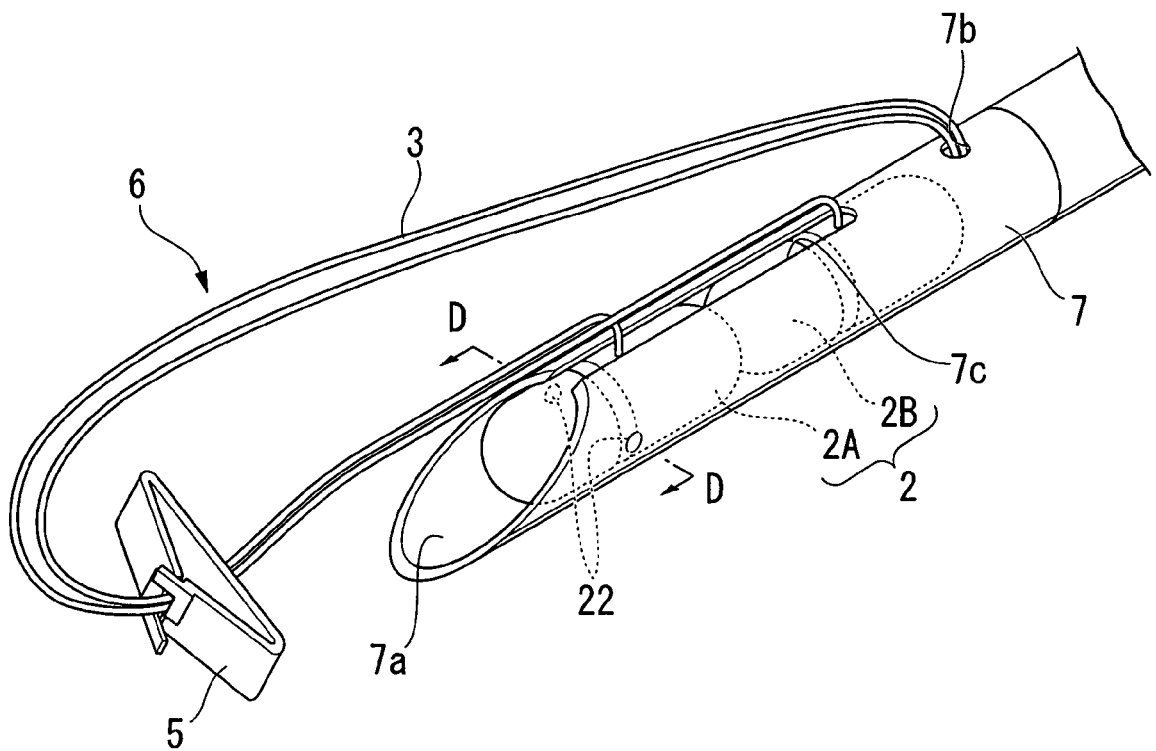
FIG. 8 is a partial perspective view of the suture instrument.
Figure 9:
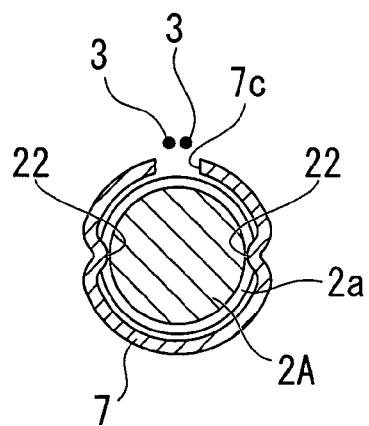
FIG. 9 is a cross-sectional view taken along line D-D of FIG. 8.

As shown in FIGS. 7 to 9, the puncture needle 7 is inserted into a channel CH1 of an endoscope insertion portion EI which is to be described later along with the outer sheath 8. The opening 7a at the distal end of the puncture needle 7 is inclined relative to the longitudinal direction of the puncture needle 7. An introduction hole 7b for introducing a loop 18 of the suture thread 3 into a cavity from the outside of the puncture needle 7 is formed on the proximal side than the distal end position of the pusher 10 on a side surface inside of the puncture needle 7. Specifically, the introduction hole is disposed at a position apart from the opening 7a by more than the total length of the first anchor 2A and the second anchor 2B arranged in series. A slit 7c having a sufficient width to let the suture thread 3 pass therethrough is disposed from the opening 7a toward the introduction hole 7b.

A restriction member 21 for restricting the movement amount of the pusher 10 toward the proximal side in the puncture needle 7 is disposed at a position closer to the proximal side than the introduction hole 7b of the puncture needle 7 so as to protrude inwardly in the diameter direction.

The restriction member 21 is disposed in the proximal end of the needle portion 7A which is closer to the proximal side than the introduction hole 7b of the puncture needle 7 so as to protrude inwardly in the diameter direction. The restriction member 21 is formed such that the slope close to the distal end of the puncture needle 7 is steep and the slope close to the proximal side is gentle. A male screw portion is formed on the outer circumferential surface of the restriction member 21 and a female screw portion capable of engaging with the male screw portion is formed at the distal end of the proximal member 7B. Accordingly, by being engaged in a screwing manner, the needle portion 7A and the proximal member 7B are coupled to each other with sufficient strength to endure a high expanding and contracting load with a simple structure.

The inner circumferential surface of the distal end side of the puncture needle 7 is provided with protrusions 22 which are to be engaged with the grooves 2a when the first anchor 2A and the second anchor 2B are housed thereinside.

The pusher 10 is made of an elongated wire. The pusher 10 is provided with an engaging portion 23 which is to be detachably engaged with the suture thread 3 which is drawn out of the slit 7c with the anchors 2 of the suture tool 6 being housed in the puncture needle 7. The engaging portion 23 is formed by curving a part of the distal end side of the pusher 10.

The outer sheath 8 includes a distal end side sheath 8A which covers the distal end side of the puncture needle 7, which houses the suture tool 6, and a proximal sheath 8B which is connected to the proximal end of the distal end side sheath 8A to cover the proximal side. The outer sheath 8 is formed of densely winded metal wires 8a in a coil shape. The distal end side sheath 8A has an inner diameter larger than that of the proximal sheath 8B so as to house the stopper 5 and the puncture needle 7.

The outer surface of the proximal sheath 8B is covered with a resin tube 24. The resin tube 24 is closely fixed onto the metal wire 8a by means of a thermal contraction. Or the resin tube 24 is formed by means of an extrusion molding by using a coil as a core which is not shown. A resin coating may be used instead of the resin tube 24.

Figure 10:
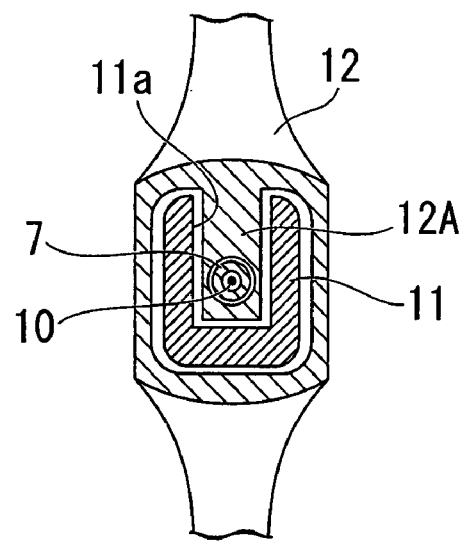
FIG. 10 is a cross-sectional view taken along line A-A of FIG. 1.
Figure 11:
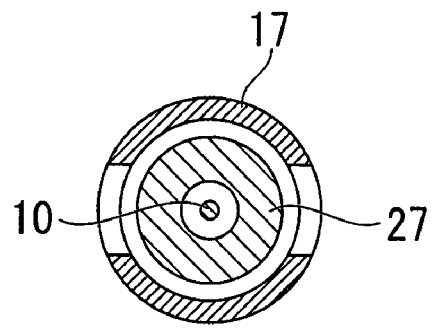
FIG. 11 is a cross-sectional view taken along line B-B of FIG. 1.

As shown in FIGS. 1, 10, and 11, a U-shaped groove 11a relative to the direction of the center axis C1 is formed in the operating portion body 11 and a finger laying portion 11A is disposed in the proximal end thereof. An adjustment stopper 25 for restricting the movement of the needle slider 12 is disposed in the distal end side of the operating portion body 11. The adjustment stopper 25 is positioned on the operating portion body 11 by using a fixing screw 26. The adjustment stopper 25 is provided with a semi-circular finger laying portion 25A.

The needle slider 12 has a protruding member 12A, which is to be engaged with the U-shaped groove 11a, and engages with the operating portion body 11 so as to advance and retreat. At the proximal end of the needle slider 12, a branch section 27 extending in the direction of a center axis C2 which is inclined relative to the center axis C1 is connected to the protruding member 12A. The needle slider 12 includes two finger laying portions 12B.

A pusher through-hole 27a, through which the proximal end side of the pusher 10 is passed, is provided on the proximal end side of the branch portion 27. A distal end of the pusher through-hole 27a is inserted by the proximal end of the proximal member 7B of the puncture needle 7 and is provided with a needle fixing portion 27A which is to be screwed similarly to the aforementioned connection of the distal end of the proximal member 7B. The branch portion 27 is formed in a cylinder shape and is inserted by a movable stopper 16 so as to advance and retreat.

The pusher operating portion 13 is formed into a cylinder shape and is connected to the proximal end of the pusher 10.

The spring member 15 has a resilient force adjusted so that the moving distance of the pusher 10 corresponds to the length of one anchor 2 when it is compressed to the maximum. The resilient force is adjusted to be smaller than the frictional force between the pusher 10 and the puncture needle 7.

The movable stopper 16 is formed into a bottomed cylindrical shell shape and is inserted to be slidable in which a bottom portion 16a is separated by a predetermined distance from the proximal end 27b of the branch section 27. A second end 15b of the spring member 15 is connected to the bottom portion 16a.

The lock member 17 protrudes from the movable stopper 16 in the longitudinal direction of the pusher operating portion 13 and is resiliently deformed in a direction in which the diameter of the movable stopper 16 decreases.

Figure 12:
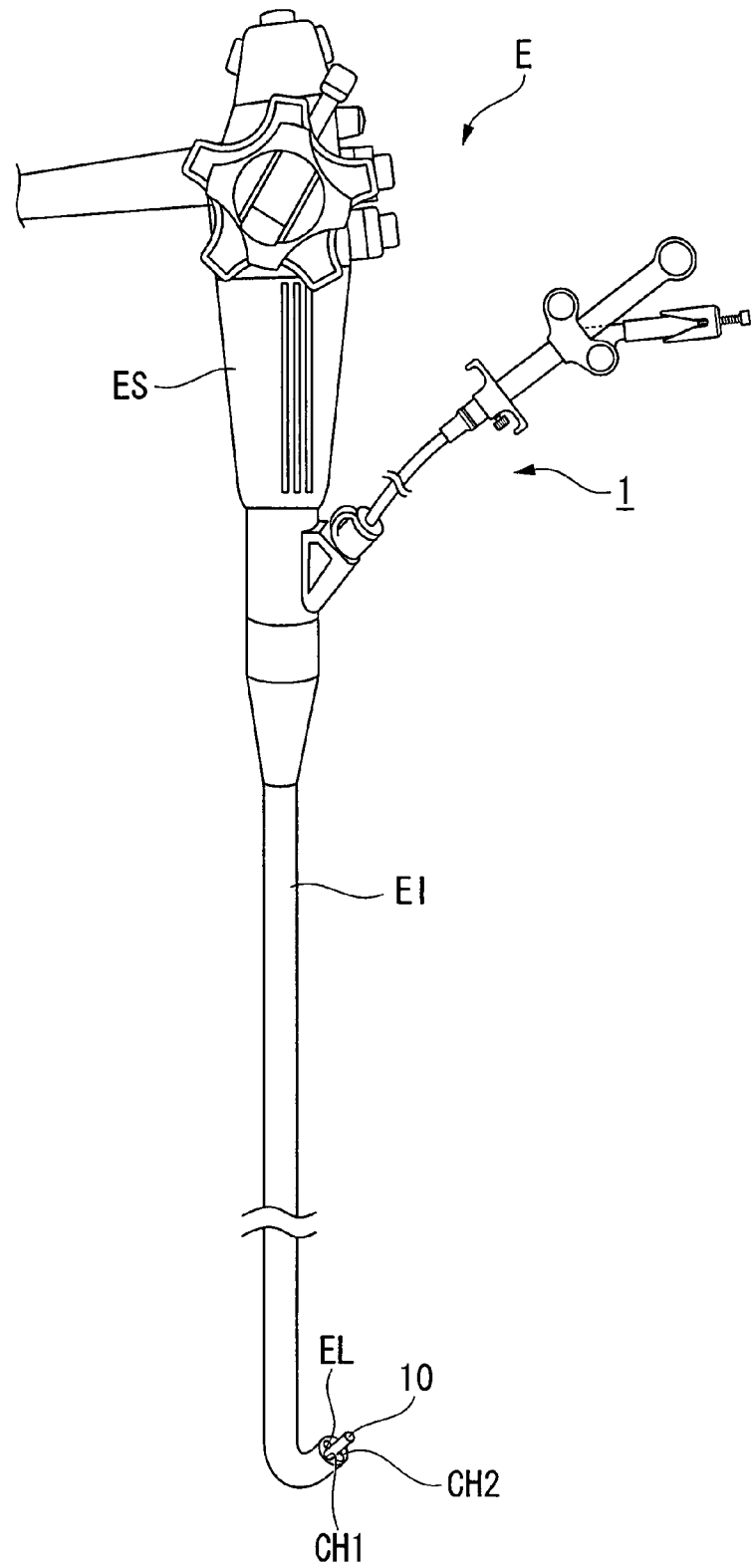
FIG. 12 is a diagram illustrating the entire general appearance of an endoscope used along with the suture instrument.

The suture instrument 1 is used along with an endoscope E, as shown in FIG. 12. The endoscope E includes an endoscope operating portion ES operated by an operator and a flexible endoscope insertion portion EI extending from the endoscope operating portion ES. The endoscope insertion portion EI has channels CH1 and CH2, into which the suture instrument 1 and the like are inserted, which are open at the distal end of the endoscope insertion portion EI. A lighting optical system EL is disposed at the distal end of the endoscope insertion portion EI.

Next, operations of the suture instrument 1 and the suture tool 6 are described along with a suturing method with reference to FIGS. 13 to 43. The stomach is shown as an example of a hollow organ.

Figure 13:
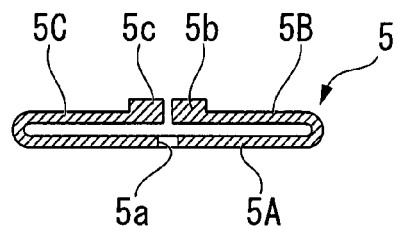
FIG. 13 is an explanatory diagram illustrating a state where a suture thread is inserted into the stopper shown in FIG. 3.
Figure 14:
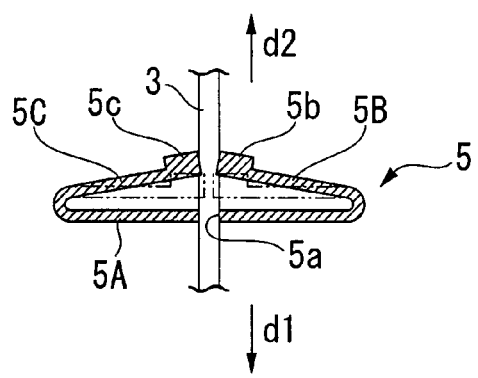
FIG. 14 is an explanatory diagram illustrating a state where a suture thread is inserted into the stopper shown in FIG. 3.

First, in the stopper 5 shown in FIG. 13, as shown in FIG. 14, the suture thread is inserted into the through-hole 5a of the base portion 5A and the suture thread 3 is inserted while the pair of bent pieces 5B and 5C is deformed in a direction in which the thick plate portions 5b and 5c are separated from each other. At this time, when the suture thread 3 is drawn in a direction d1 of the base portion 5A, the thick plate portions 5b and 5c also move in the direction d1 and the distance between the thick plate portions 5b and 5c decreases to tightly fasten and lock the suture thread 3, thereby restricting the movement of the suture thread 3.

That is, when a force acts on the suture thread 3 in a direction in which the anchors 2 are separated from the stopper 5, the pair of bent pieces 5B and 5C are moved to be closer to each other, thereby locking the movement of the suture thread 3. That is, even when an anastomosis object to be anastomosed by the stopper 5 and the anchors 2 pushes the stopper 5 in a direction d2 toward the other end of the suture thread 3, the thick plate portions 5B and 5c tightly fasten the suture thread 3 and locks the position of the stopper 5 relative to the suture thread 3. As a result, the stopper 5 is not moved in the direction d2.

Figure 15:
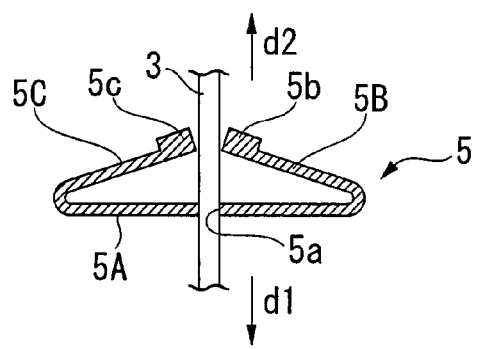
FIG. 15 is an explanatory diagram illustrating a state where a suture thread is inserted into the stopper shown in FIG. 3.

On the other hand, as shown in FIG. 15, when the stopper 5 is moved to be closer to the anchors 2, that is, when the suture thread 3 is drawn in the direction d2 opposite to the base portion 5A, the thick plate portions 5b and 5c also move in the direction d2 (in a direction in which they are separated from each other), thereby releasing the fastening to the suture thread 3. That is, the movement of the suture thread 3 in the direction in which the anchors 2 and the stopper 5 becomes closer to each other is allowed. That is, when the stopper 5 is pressed to the anastomosis object, that is, when the stopper 5 is moved in the direction d1 of one end of the suture thread 3, the thick plate portions 5b and 5c are opened and the fastening of the thick plate portions 5b and 5c to the suture thread 3 is released.

Figure 16:
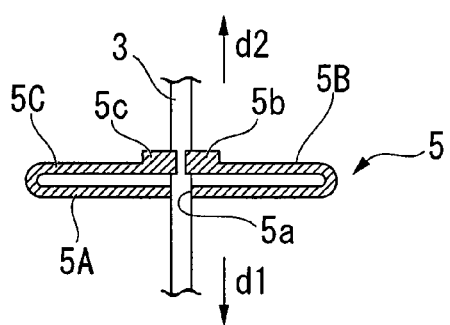
FIG. 16 is an explanatory diagram illustrating a state where a suture thread is inserted into the stopper shown in FIG. 3.

As shown in FIG. 16, the stopper 5 is compulsorily moved in the direction d2 by the pressure from the anastomosis object. At this time, the base portion 5A of the stopper and the pair of bent portions 5B and 5C become substantially parallel to each other. Since this state is similar to the molded state, the bending stress hardly occurs in the pair of bent pieces 5B and 5C. Accordingly, the fastening force on the suture thread 3 is maintained without moving relative to the anastomosis object.

Figure 17:
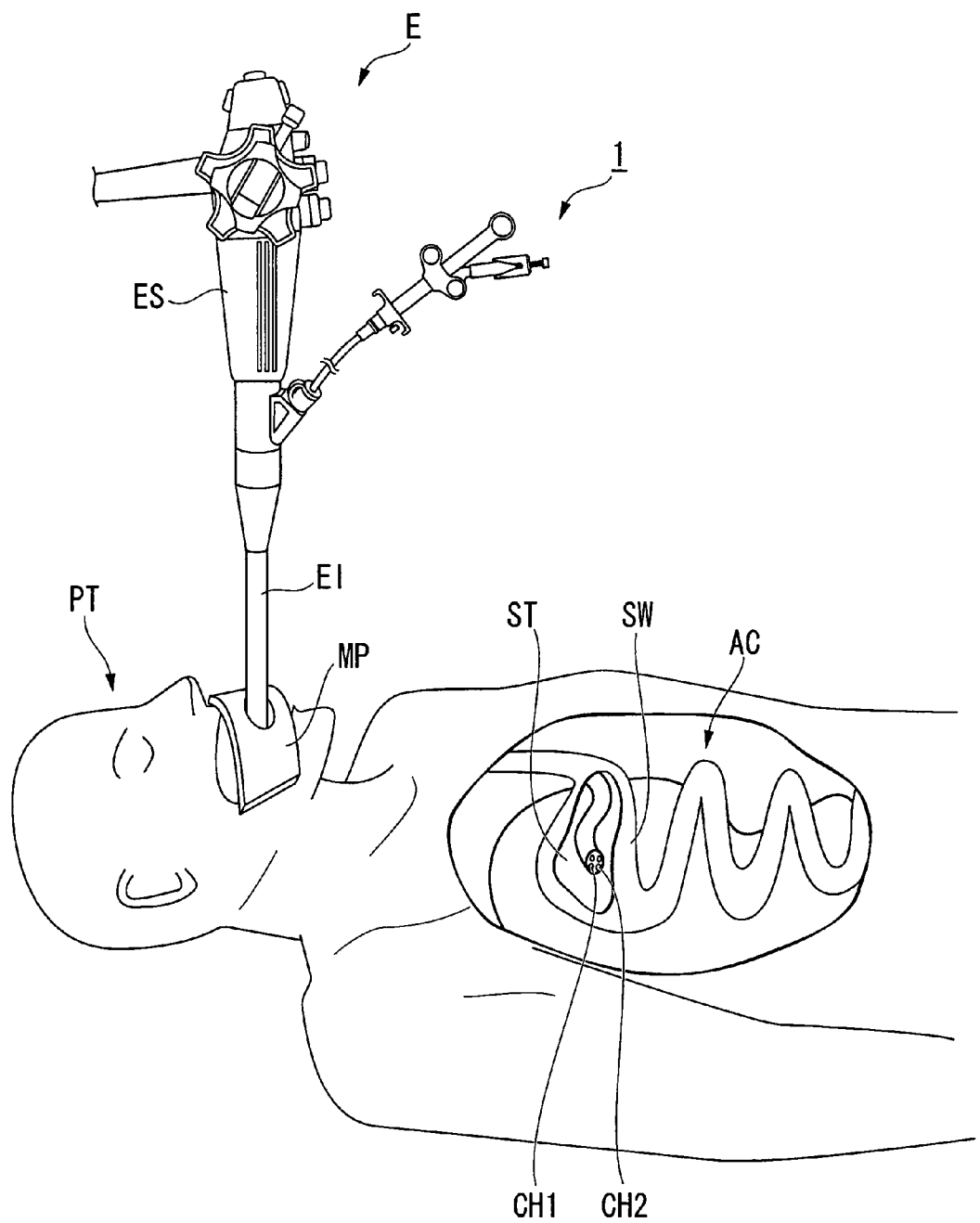
FIG. 17 is an explanatory diagram illustrating an operation of the suture instrument.
Figure 18:
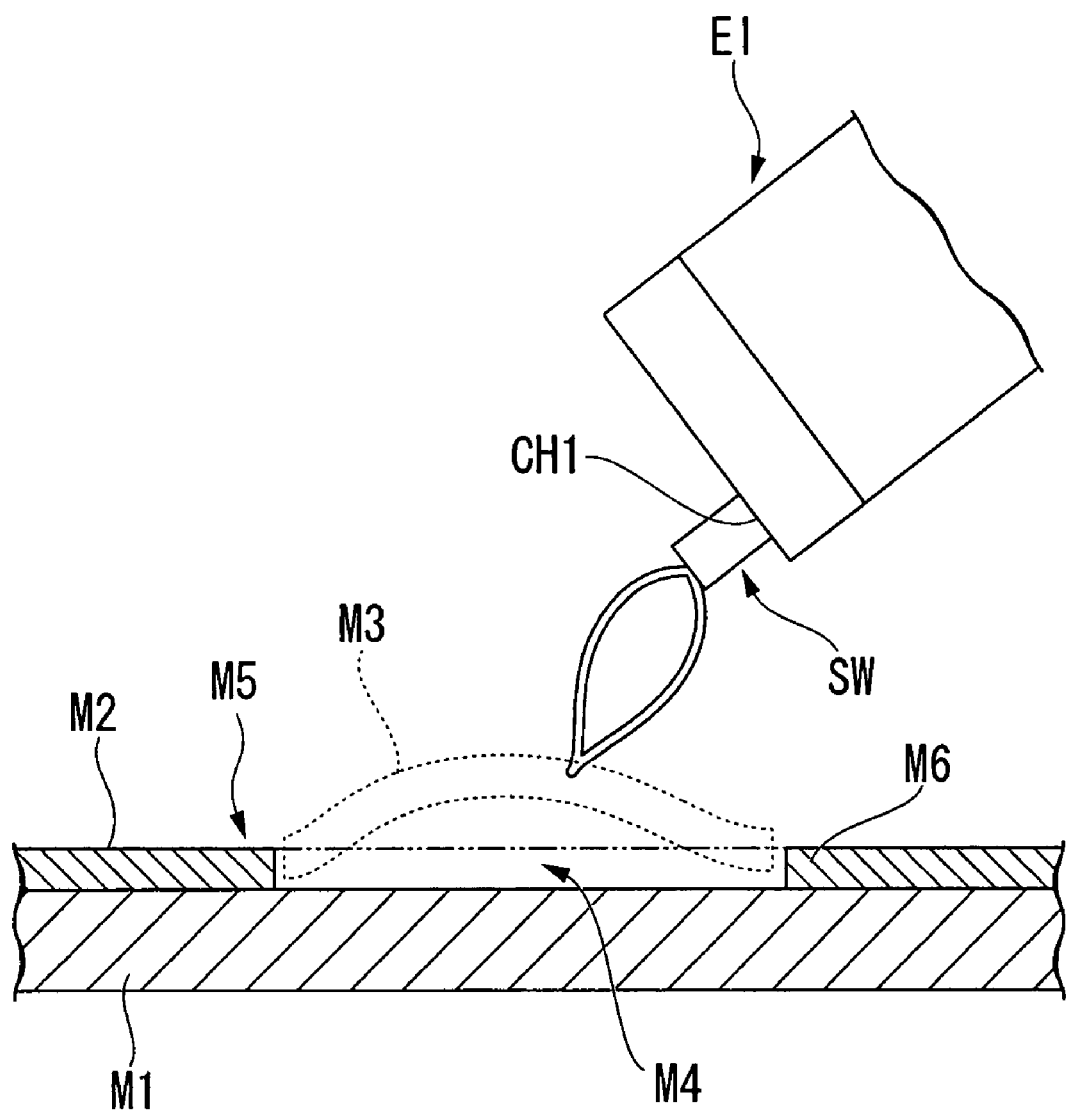
FIG. 18 is an explanatory diagram illustrating an operation of the suture instrument.

Next, as shown in FIG. 17, the endoscope insertion portion EI is inserted into a mouth of a patient PT wearing a mouthpiece MP and the distal end of the endoscope insertion portion EI is curved. As shown in FIG. 18, an incising treatment instrument SW such as a snare is inserted into the channel CH1 of the endoscope insertion portion EI to cut off a mucous membrane M3 including a pathological lesion.

Figure 19:
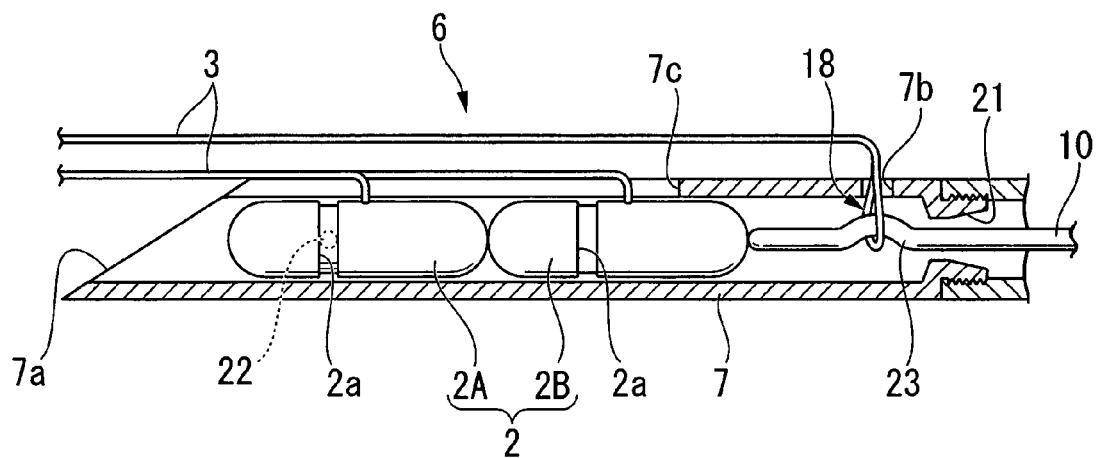
FIG. 19 is an explanatory diagram illustrating an operation of the suture instrument.

On the other hand, as shown in FIG. 19, the first anchor 2A and the second anchor 2B of the suture tool 6 are housed in series in the puncture needle 7 and the protrusion 22 is engaged with the groove 2a of the first anchor 2A. The suture thread 3 is protruded from the slit 7c and the loop 18 is introduced again into the puncture needle 7 from the introduction hole 7b. The loop 18 is inserted through the pusher 10 to engage with the engaging portion 23, thereby maintaining the stopper 5 housed in the puncture needle 7.

After cutting off the mucous membrane M3, the suture instrument 1 is inserted into the channel CH1 instead of the incising treatment instrument SW and the distal end of the outer sheath 8 is protruded from the distal end of the channel CH1.

Figure 20:
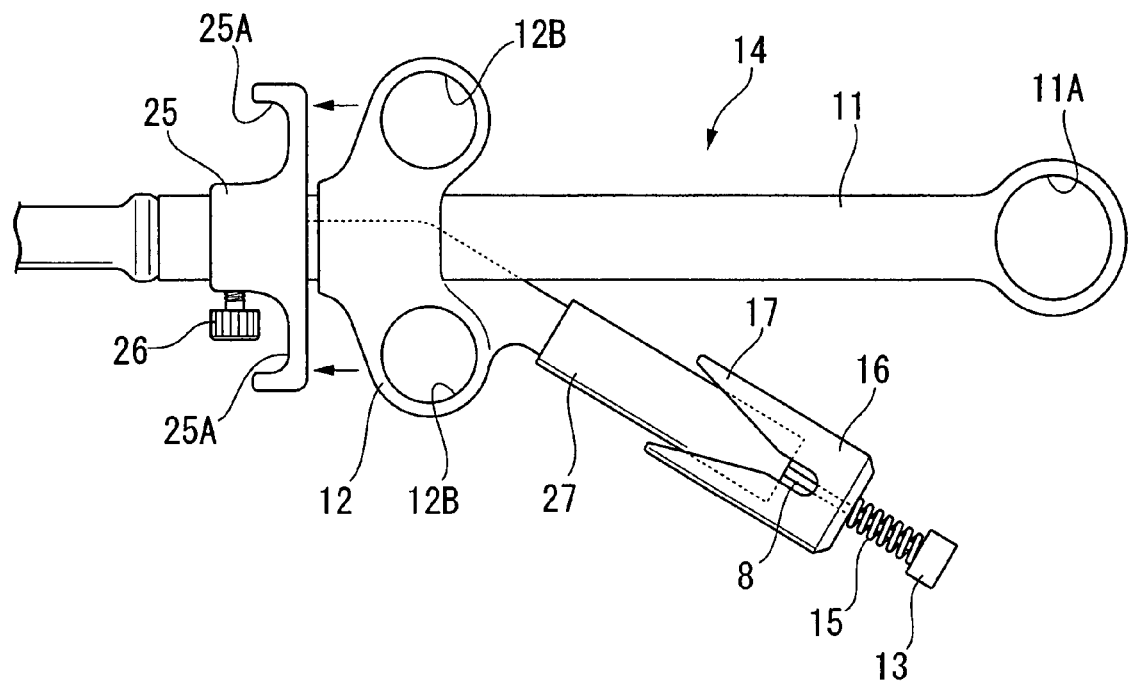
FIG. 20 is an explanatory diagram illustrating an operation of the suture instrument.
Figure 21:
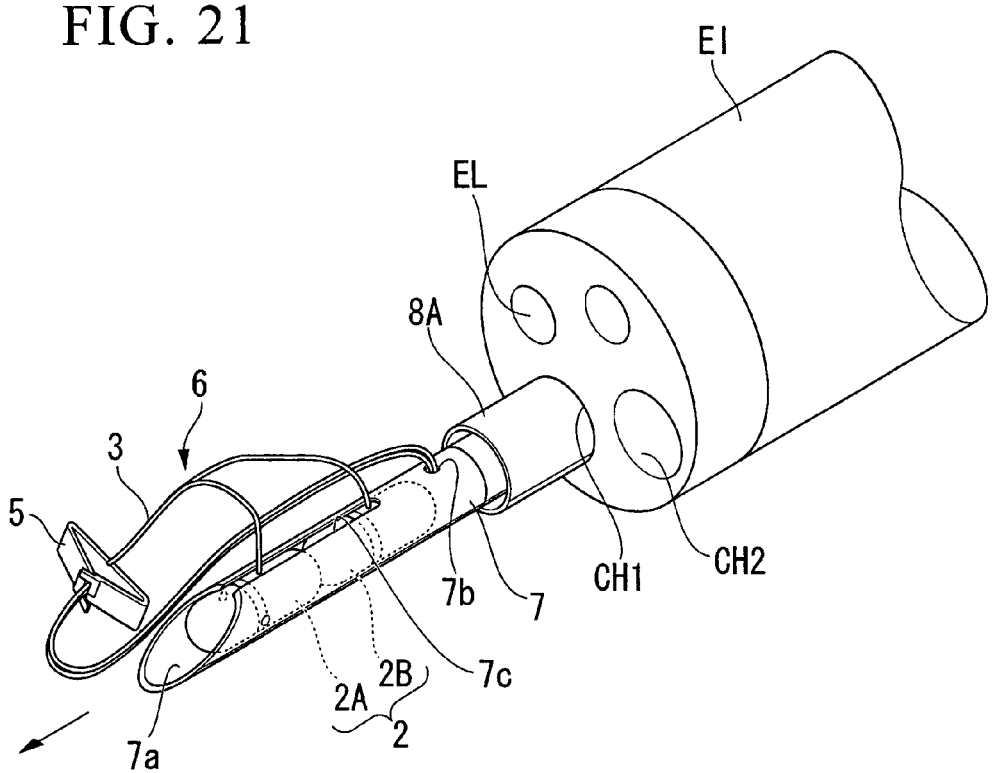
FIG. 21 is an explanatory diagram illustrating an operation of the suture instrument.

In this state, as shown in FIG. 20, the needle slider 12 is advanced relative to the operating portion body 11 and as shown in FIG. 21, the puncture needle 7 is protruded from the outer sheath 8. At this time, the needle slider 12 is moved forward by means of passing one's thumb through the finger laying portion 11A, passing one's index finger, a middle finger, or a ring finger through the finger laying portion 12B, and opening both fingers. Alternatively, the needle slider 12 may be moved forward by means of laying one's thumb on the finger laying portion 12B, laying one's index finger, a middle finger, or a ring finger on the semi-circular finger laying portion 25A, and closing both fingers. Since this closing operation can permit a finer adjustment than the opening operation and thus can apply a force more conveniently, the protruding amount and the speed of the puncture needle 7 from the outer sheath can be more easily controlled.

Figure 22:
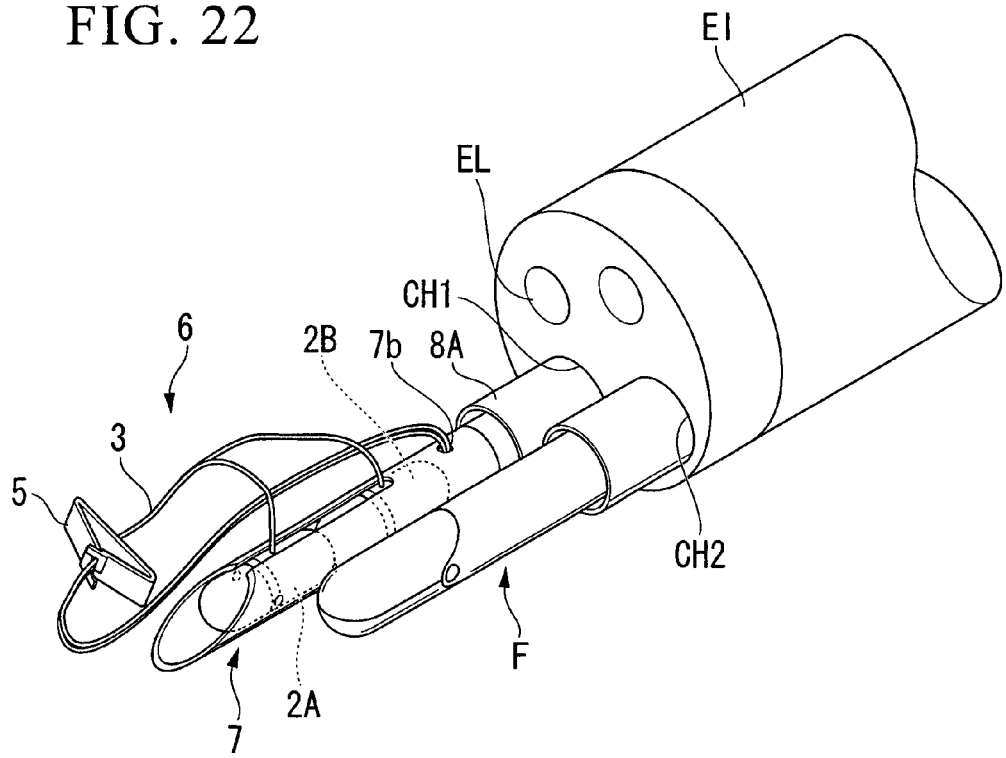
FIG. 22 is an explanatory diagram illustrating an operation of the suture instrument.
Figure 23:
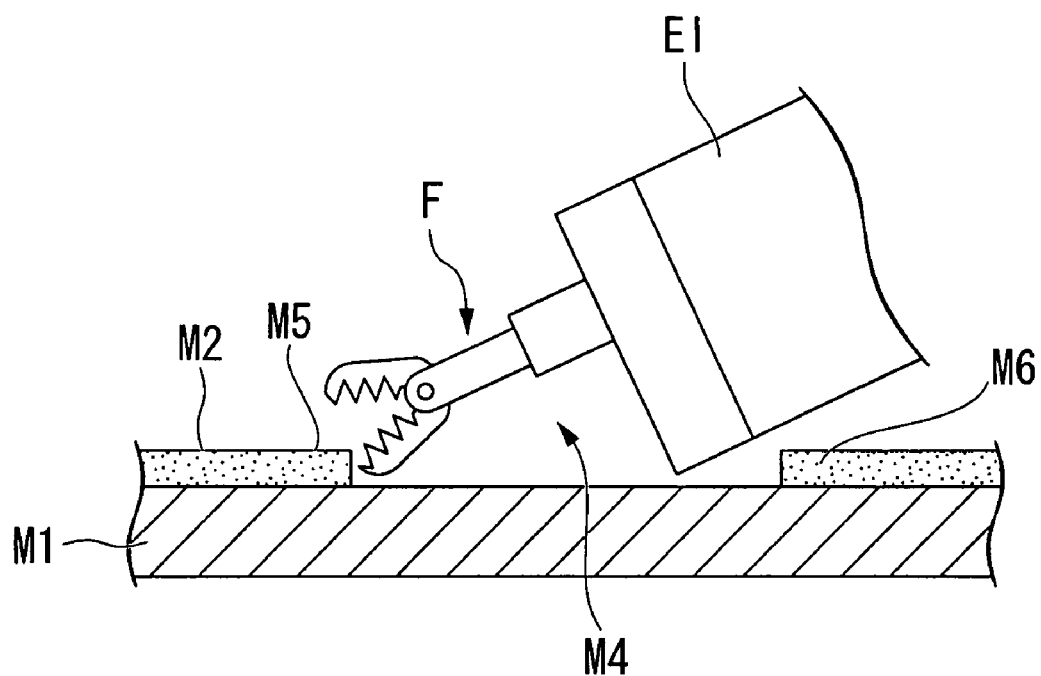
FIG. 23 is an explanatory diagram illustrating an operation of the suture instrument.

Next, as shown in FIG. 22, a pair of forceps F is inserted into the channel CH2 and is protruded from the distal end thereof, grasps a distal cut end M5 of a mucous-membrane defect portion M4 and pulls and holds up the distal cut end in a direction apart from the mucous-membrane defect portion M4 as shown in FIG. 23.

Figure 24:
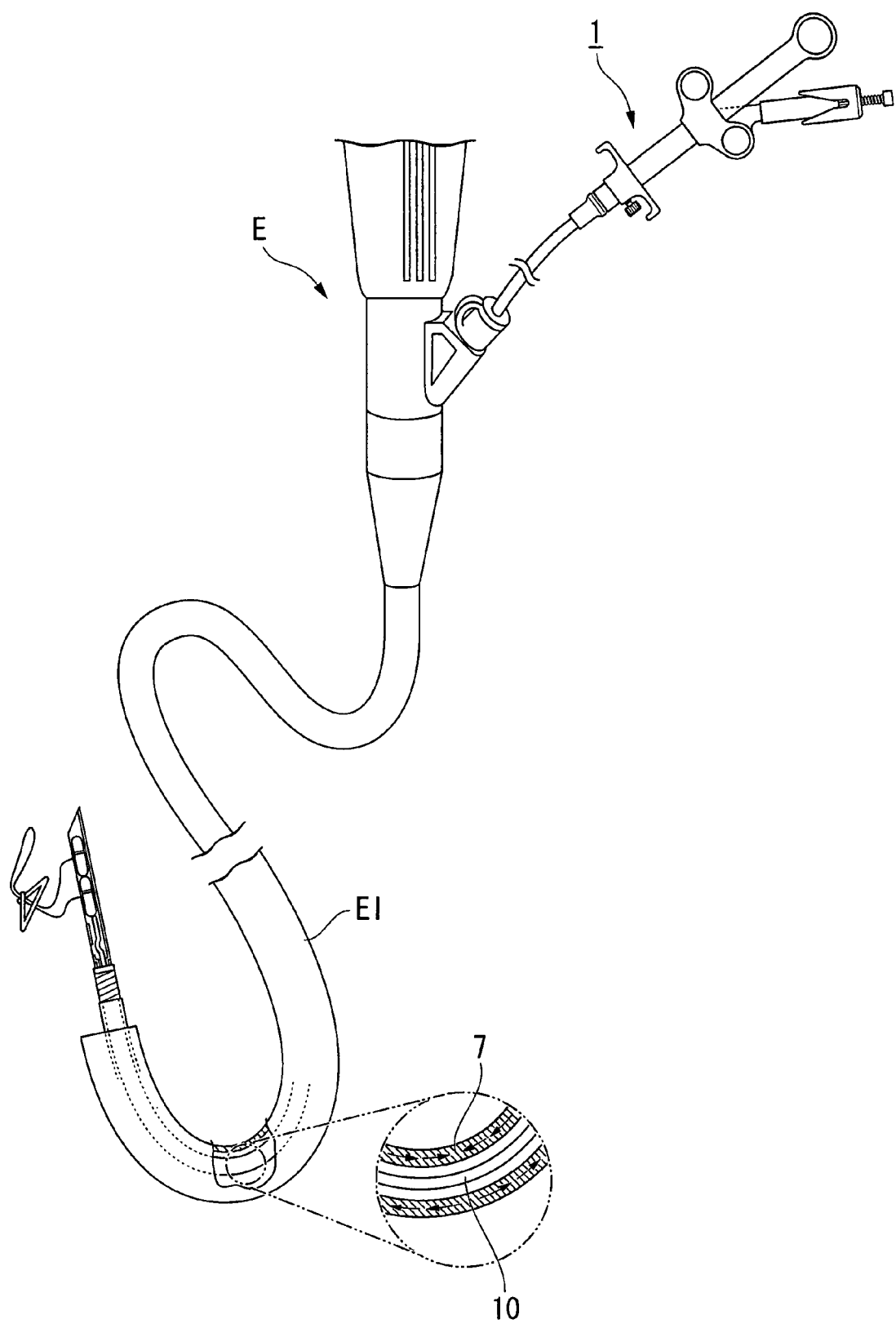
FIG. 24 is an explanatory diagram illustrating an operation of the suture instrument.

In this state, as shown in FIG. 24, the endoscope insertion section EI is curved to define the puncture direction of the puncture needle 7. At this time, since the proximal member 7B of the puncture needle 7 is formed of a soft tube the outer portion, in which the pusher 10 as an axis, expands in the curved direction. On the other hand, since the pusher 10 is a wire having a high rigidity and a small diameter, the pusher 10 does not expand with the curving operation. Accordingly, the engaging portion 23 of the pusher 10 engages with the restriction member 21 in the puncture needle 7 and thus the pusher operating portion 13 is relatively drawn toward the branch portion 27 along with the movable stopper 16.

Figure 25:
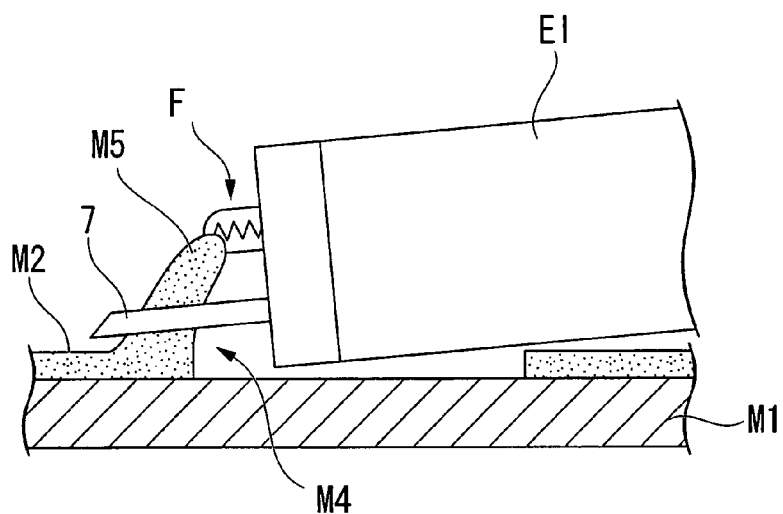
FIG. 25 is an explanatory diagram illustrating an operation of the suture instrument.

Thereafter, the needle slider 12 is advanced relative to the operating portion body 11 until coming in contact with the adjustment stopper 25 so as to protrude the puncture needle 7 from the distal end of the outer sheath 8. In this way, as shown in FIG. 25, by advancing the entire suture instrument 1 or the endoscope insertion portion EI, the puncture needle 7 penetrates the mucous membrane M5 which is supported by means of operations of the pair of forceps F and the endoscope.

Figure 26:
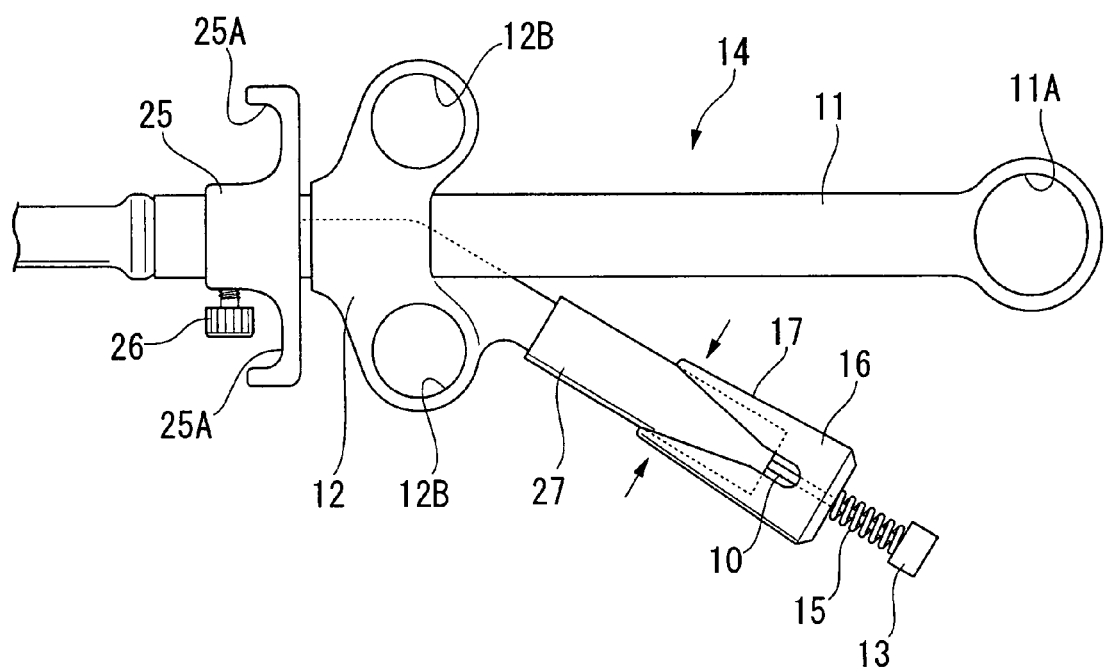
FIG. 26 is an explanatory diagram illustrating an operation of the suture instrument.
Figure 27:
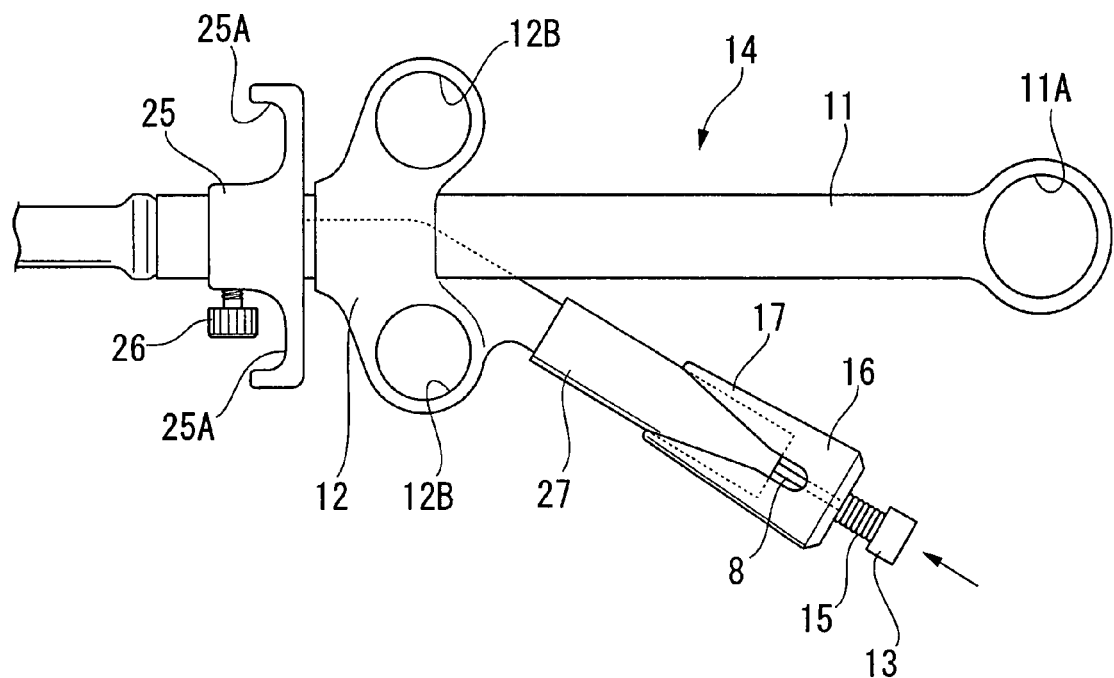
FIG. 27 is an explanatory diagram illustrating an operation of the suture instrument.
Figure 28:
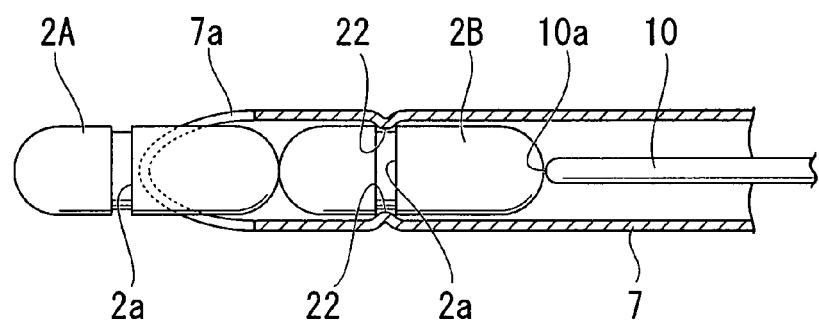
FIG. 28 is an explanatory diagram illustrating an operation of the suture instrument.

Next, as shown in FIG. 26, the movable stopper 16 and the branch section 27 are fixed to each other by grasping the lock member 17 of the movable stopper 16 along with the branch section 27. As shown in FIG. 27, the spring member 15 is compressed by moving the pusher operating portion 13 toward the distal end side. At this time, the pusher 10 moves relative to the puncture needle 7 by the length of one anchor. Accordingly, the protrusion 22 and the groove 2a of the first anchor 2A are disengaged from each other and thus the second anchor 2B advances, as shown in FIG. 28, thereby extruding the first anchor 2A, which is in face contact, toward the front end of the puncture needle 7. Then, the groove 2a of the second anchor 2B newly engages with the protrusion 22. As a result, the first anchor 2A drops to the rear side of the mucous membrane M5. When the puncture needle 7 is pulled out of the mucous membrane M5, the suture thread 3 penetrates the mucous membrane M5 and the first anchor 2A is detained in the distal side of the mucous-membrane defect portion M4.

Figure 29:
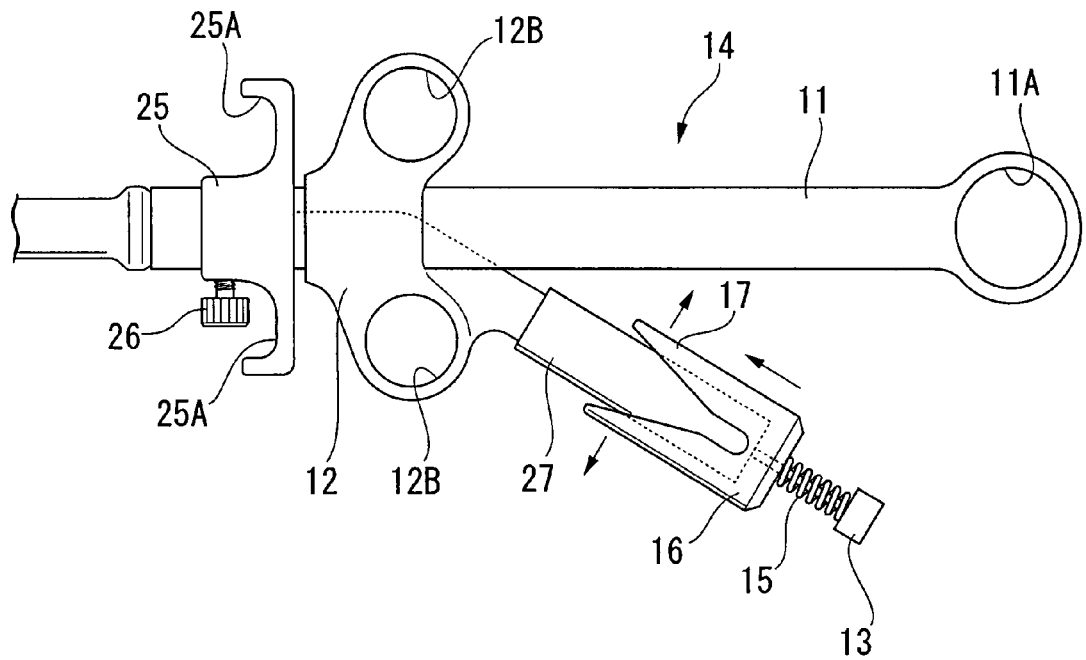
FIG. 29 is an explanatory diagram illustrating an operation of the suture instrument.

Subsequently, the lock member 17 is released and thus the movable stopper 16 is restored to the original shape. Here, the resilient restoring force of the spring member 15 is set smaller than the frictional force generated over the entire length between the pusher 10 and the puncture needle 7. Accordingly, while the spring member 15 is restored to the original length without a relative movement between the pusher 10 and the puncture needle 7, the movable stopper 16 advances relative to the branch portion 27, as shown in FIG. 29.

Figure 30:
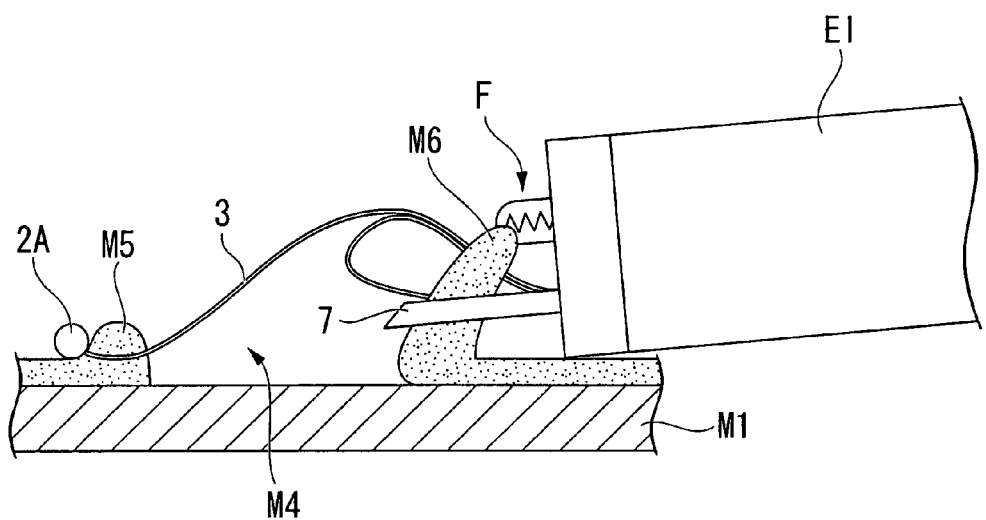
FIG. 30 is an explanatory diagram illustrating an operation of the suture instrument.

Next, the front end of the endoscope insertion portion EI is moved to the place where the second anchor 2B is detained. Similarly to the first anchor 2A, as shown in FIG. 30, the end portion of a mucous membrane M6 in the proximal side which is almost symmetric with the mucous membrane M5 with the mucous-membrane defect portion M4 interposed therebetween is grasped and supported by the forceps F. By advancing the entire suture instrument 1 or the endoscope insertion portion EI with the puncture needle 7 protruding from the distal end of the outer sheath 8, the puncture needle 7 penetrates the supported mucous membrane M6.

Figure 31:
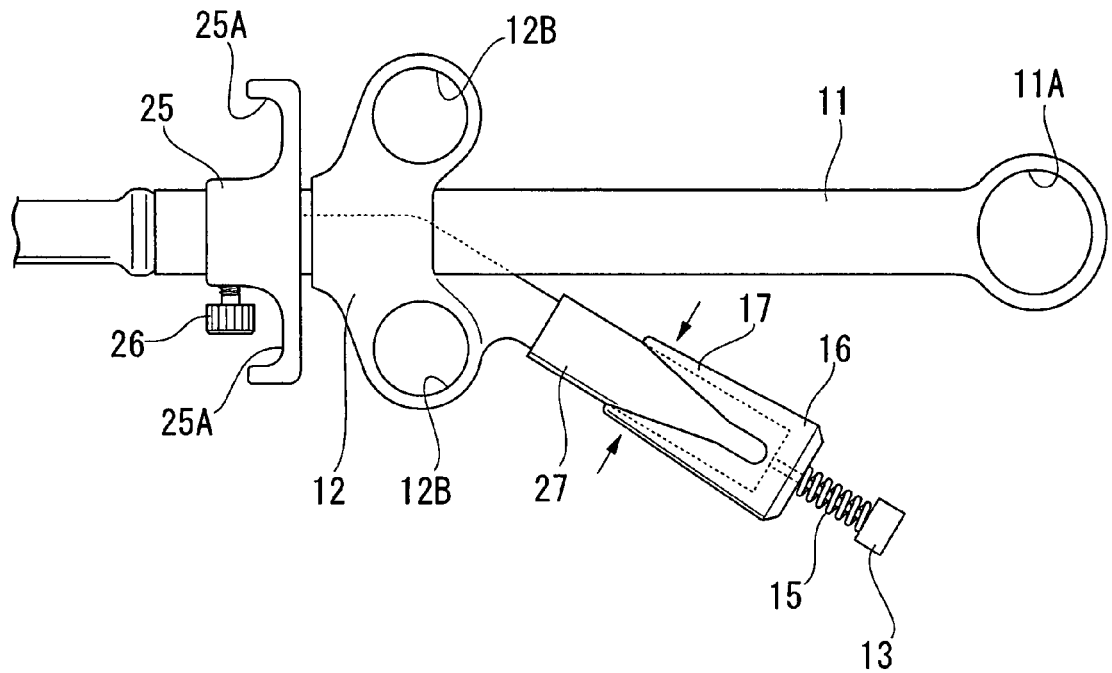
FIG. 31 is an explanatory diagram illustrating an operation of the suture instrument.
Figure 32:
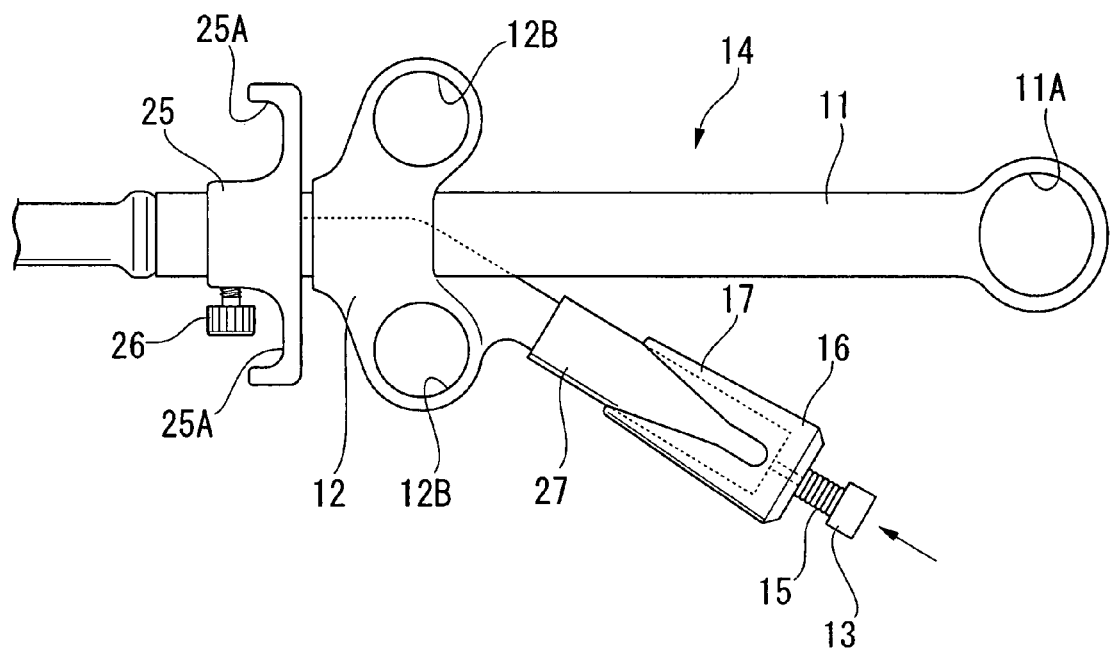
FIG. 32 is an explanatory diagram illustrating an operation of the suture instrument.
Figure 33:
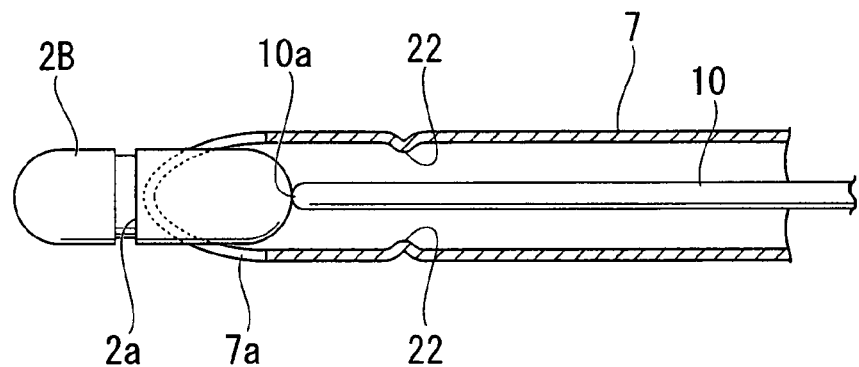
FIG. 33 is an explanatory diagram illustrating an operation of the suture instrument.
Figure 34:
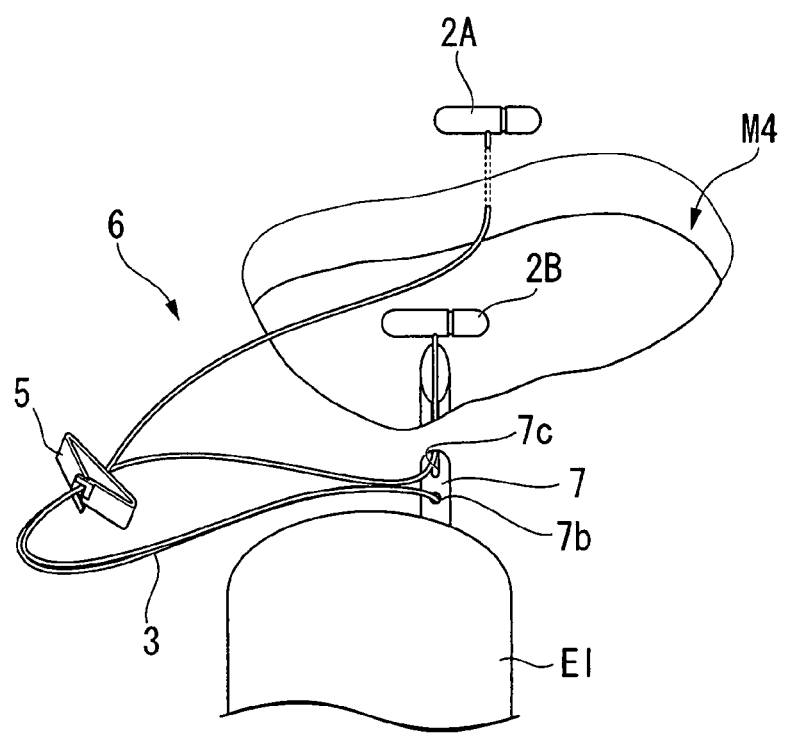
FIG. 34 is an explanatory diagram illustrating an operation of the suture instrument.

Here, as shown in FIG. 31, the lock member 17 is grasped again and deformed to come in contact with the branch portion 27. And as shown in FIG. 32, the pusher operating portion 13 is moved relative to the movable stopper 16 to compress the spring member 15. Accordingly, as shown in FIG. 33, the protrusion 22 and the groove 2a of the second anchor 2B are disengaged from each other and thus the second anchor 2B is discharged to the rear side of the mucous membrane M6. When the puncture needle 7 is pulled out of the mucous membrane M6, the suture thread 3 penetrates the mucous membrane M6 and the second anchor 2B is detained in the proximal side of the mucous-membrane defect portion M4, as shown in FIG. 34.

Figure 35:
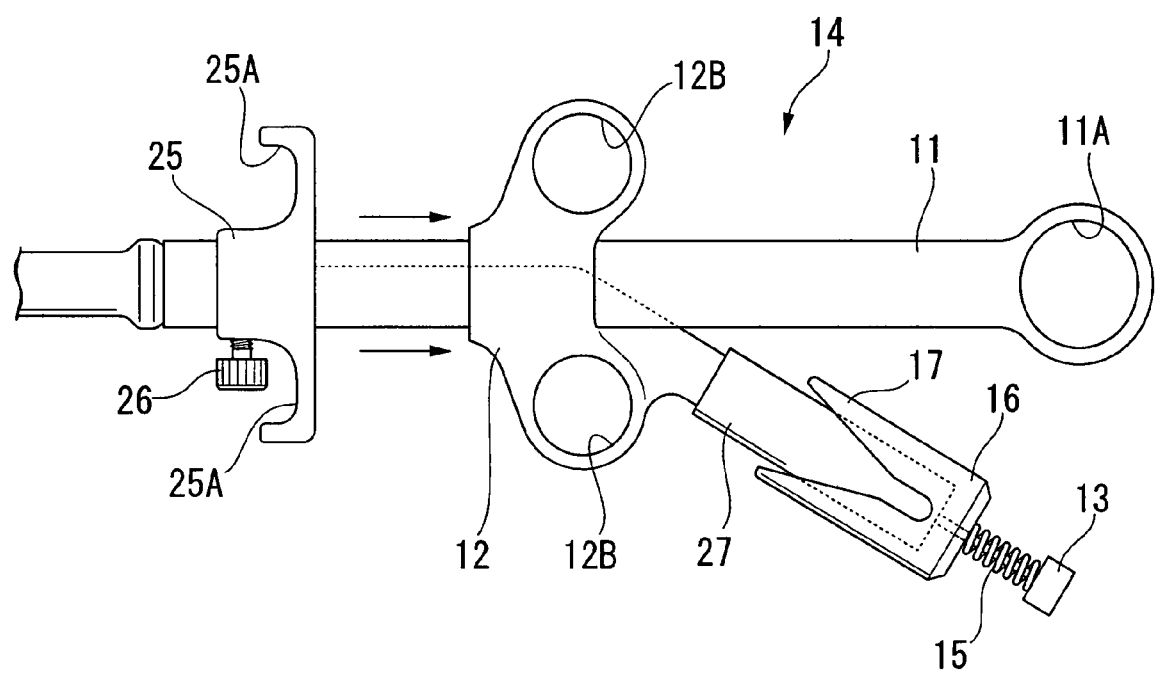
FIG. 35 is an explanatory diagram illustrating an operation of the suture instrument.
Figure 36:
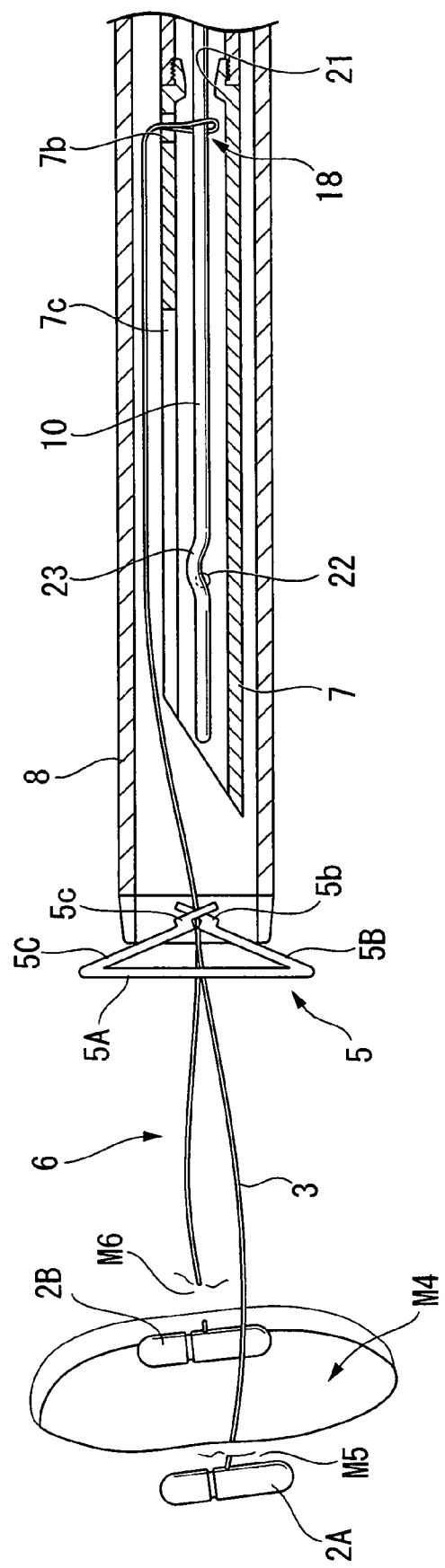
FIG. 36 is an explanatory diagram illustrating an operation of the suture instrument.
Figure 37:
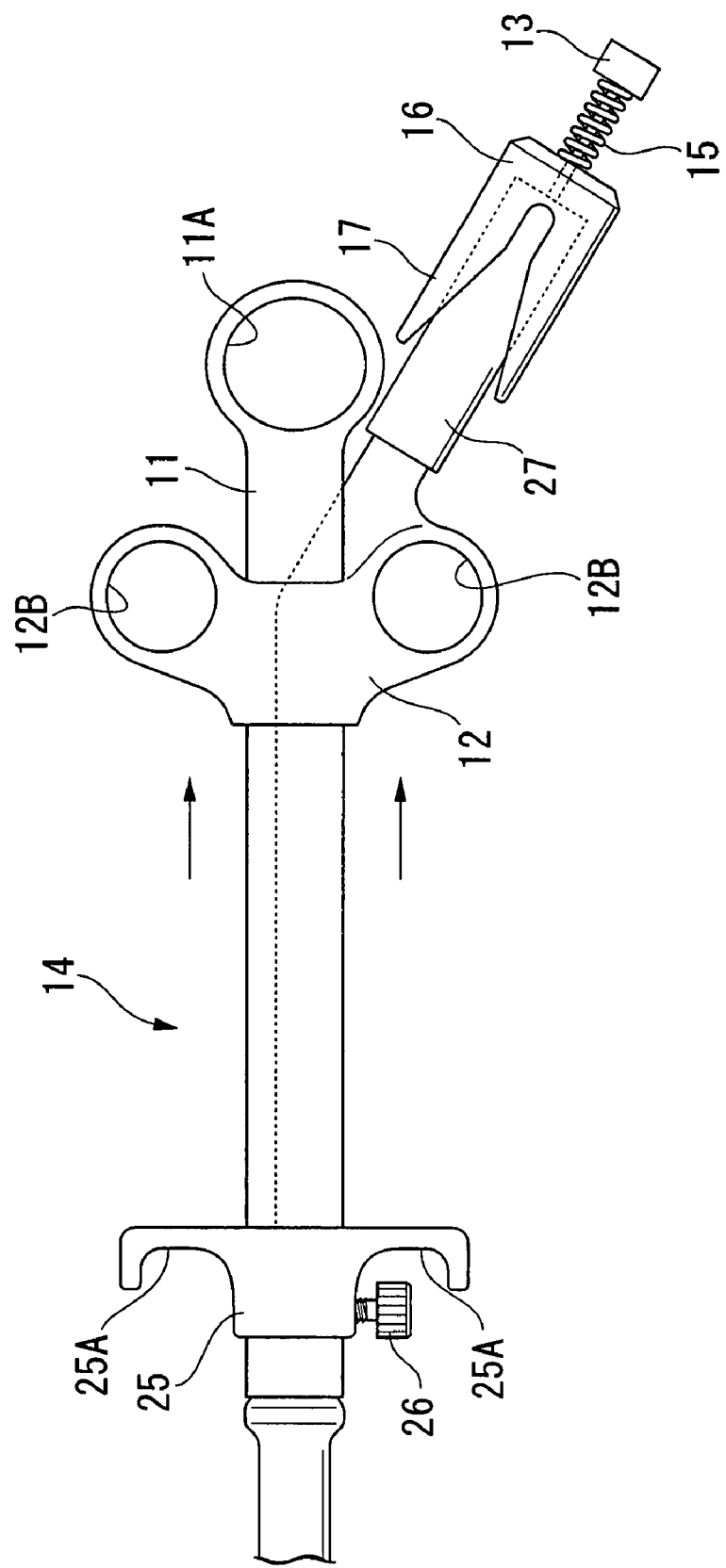
FIG. 37 is an explanatory diagram illustrating an operation of the suture instrument.
Figure 38:
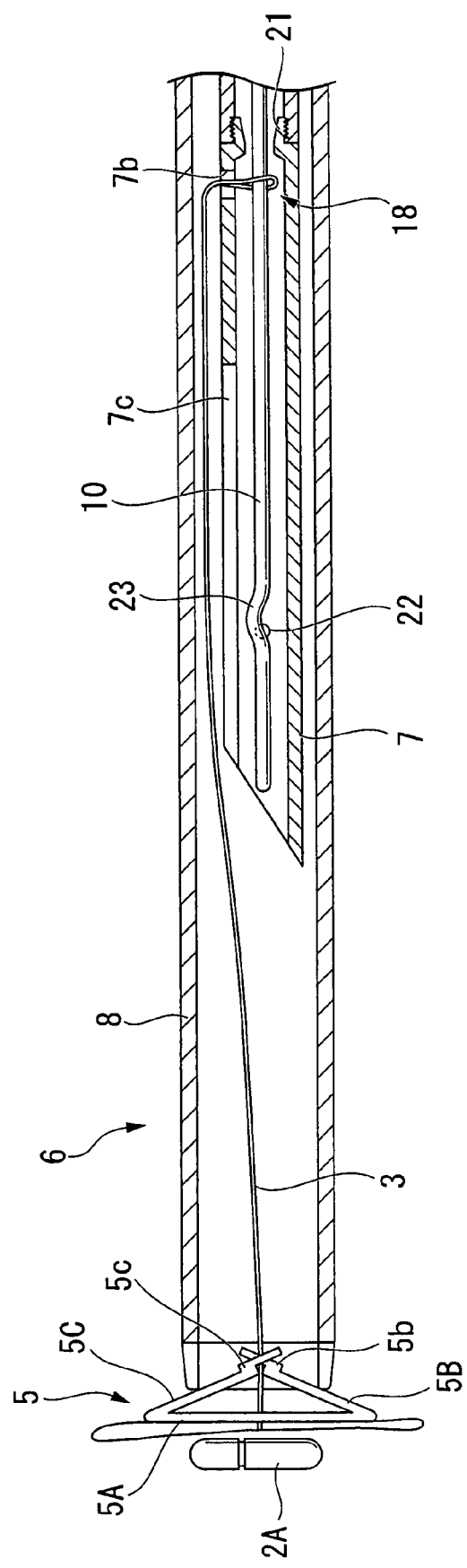
FIG. 38 is an explanatory diagram illustrating an operation of the suture instrument.

Next, as shown in FIG. 35, the needle slider 12 is retreated toward the proximal side relative to the operating portion body 11. Accordingly, the puncture needle 7 is relatively drawn into the outer sheath 8 and the distal end of the outer sheath 8 comes in contact with the stopper 5 of the suture tool 6, as shown in FIG. 36. Further as shown in FIG. 37, by moving the needle slider 12 to the proximal side, the distance between the stopper 5 and the anchors 2 is reduced. The reduction in distance between the anchors 2A and 2B allows the mucous membranes M5 and M6 anchored by the anchors 2A and 2B to be drawn closer to each other. Finally, as shown in FIG. 38, the stopper 5 comes in contact with the mucous membranes M5 and M6 and is tightly fastened, thereby reducing the mucous-membrane defect portion M4.

Figure 39:
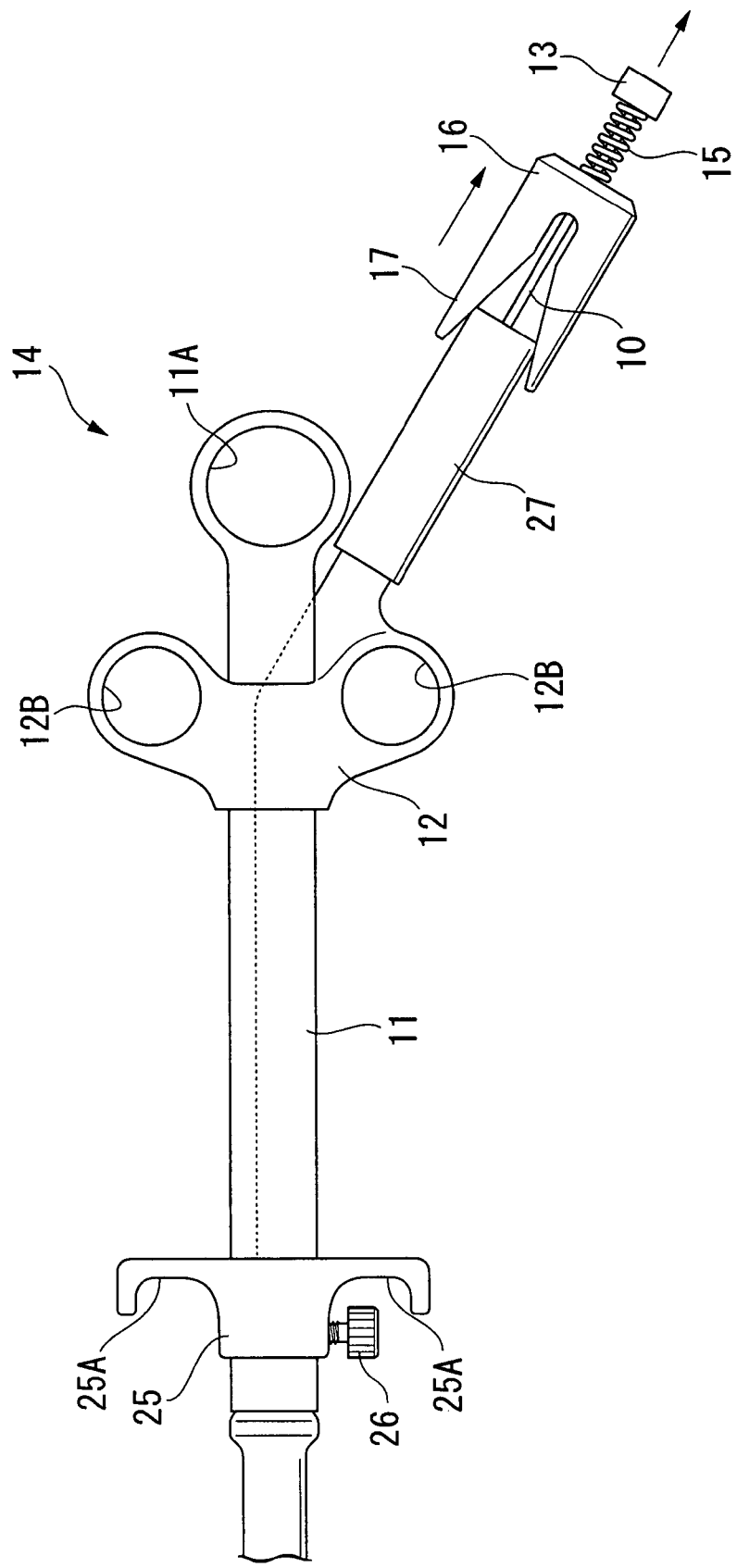
FIG. 39 is an explanatory diagram illustrating an operation of the suture instrument.
Figure 40:
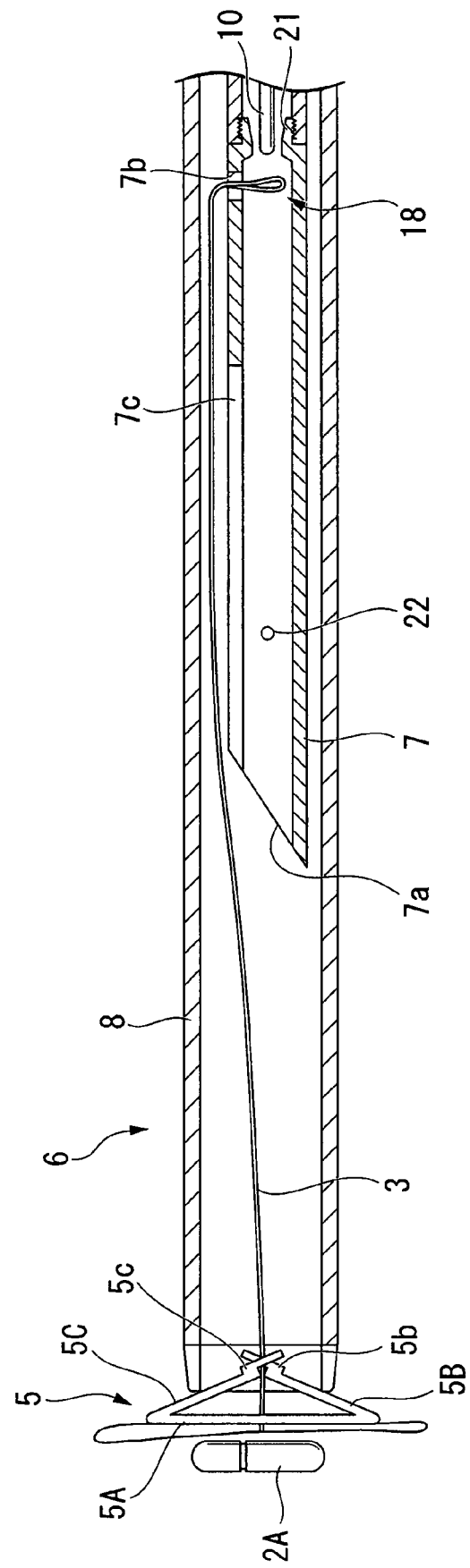
FIG. 40 is an explanatory diagram illustrating an operation of the suture instrument.
Figure 41:
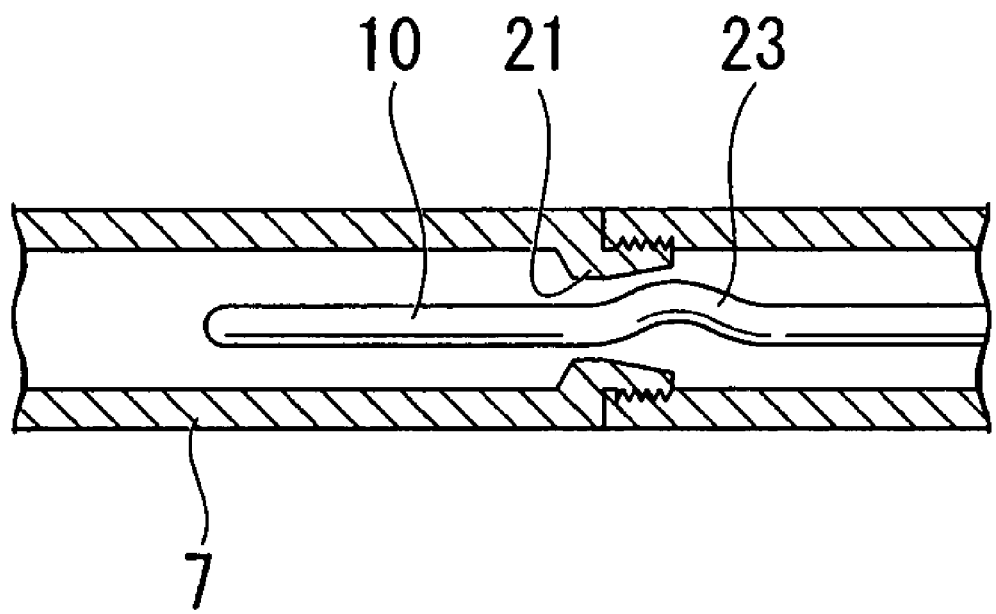
FIG. 41 is an explanatory diagram illustrating an operation of the suture instrument.
Figure 42:
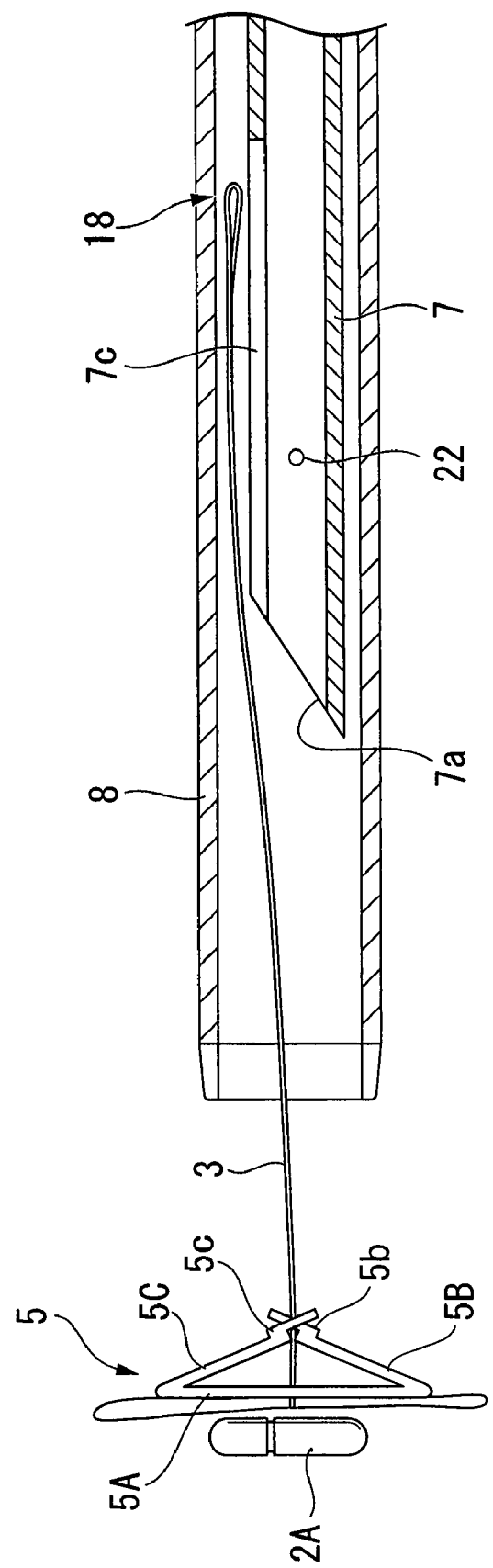
FIG. 42 is an explanatory diagram illustrating an operation of the suture instrument.
Figure 43:
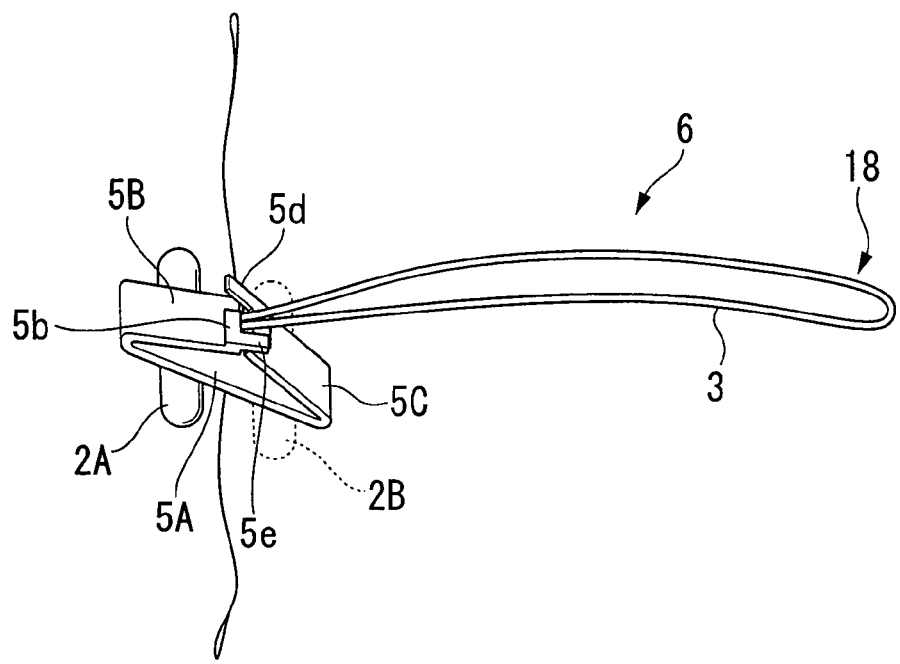
FIG. 43 is an explanatory diagram illustrating an operation of the suture instrument.
Figure 44:
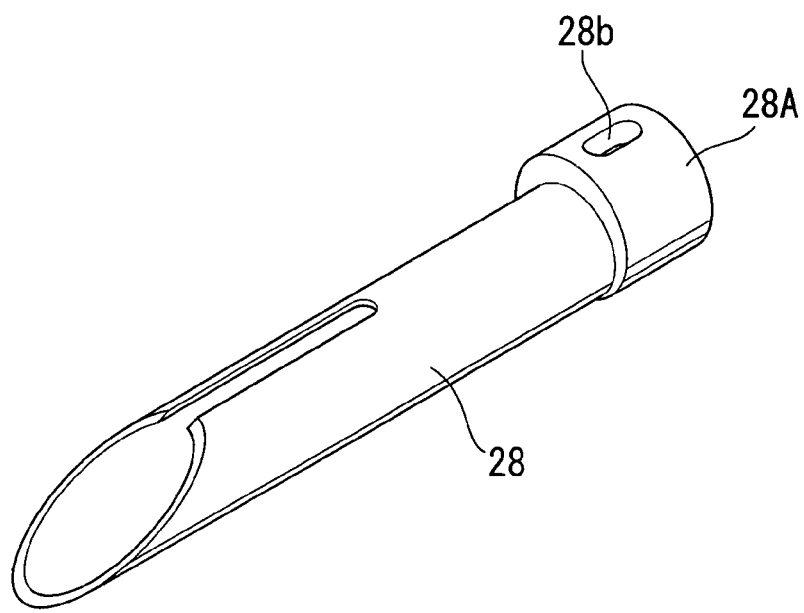
FIG. 44 is a perspective view illustrating a modified example of a suture needle of the suture instrument.
Figure 45:
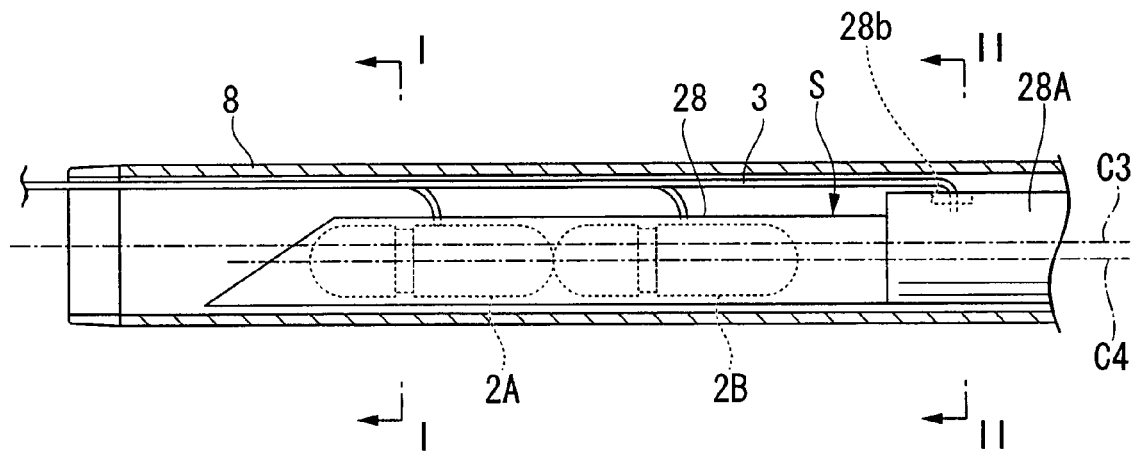
FIG. 45 is a partially sectional view illustrating a modified example of the suture needle of the suture instrument.
Figure 46:
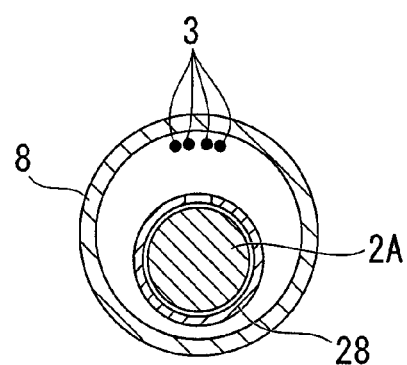
FIG. 46 is a cross-sectional view taken along line I-I of FIG. 45.
Figure 47:
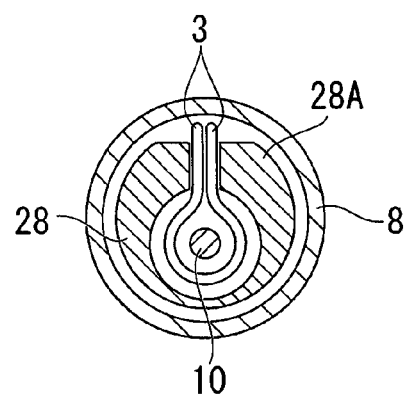
FIG. 47 is a cross-sectional view taken along line II-II of FIG. 45.

As shown in FIG. 39, the movable stopper 16 is retreated toward the proximal side relative to the branch portion 27. At this time, as shown in FIGS. 40 and 41, the loop 18 of the suture thread 3 gets off from the engaging portion 23 of the pusher 10 and the engaging portion 23 is resiliently deformed so as to go over the restriction member 21, thereby moving the pusher 10 to the proximal side relative to the puncture needle 7. Here, when the suture instrument 1 or the endoscope insertion section EI is retreated from the mucous-membrane defect portion M4, the loop 18 is drawn from the introduction hole 7b of the puncture needle 7 to the outside of the puncture needle 7, as shown in FIG. 42. In this way, as shown in FIG. 43, the suture tool 6 is separated from the suture instrument 1, in which the suture thread 3 is maintained not to be loosened by the stopper 5, thereby detaining the suture tool 6.

According to the suture instrument 1, even when the sheath 9 is curved, it is possible to move the pusher operating section 13 relative to the operating section body 11 along with the expansion and contraction of the sheath 9 by setting the movable stopper 16 to the movable state and setting the spring member 15 to the expanded state. By setting the movable stopper 16 to the fixed state and setting the spring member 15 to the contracted state by using the lock member 17, it is possible to move the position of the distal end 10a of the pusher 10 relative to the sheath 9 by a predetermined distance. Accordingly, regardless of before or after the curvedness of the sheath 9, it is possible to precisely advance and retreat the pusher 10 relative to the sheath 9 by a predetermined distance with a simple operation.

At this time, by grasping the lock member 17 to come in contact with the branch portion 27, it is possible to fix the movable stopper 16 relative to the operating portion body 11. On the other hand, when the lock member 17 is not deformed, the movable stopper 16 can be set to the movable state relative to the branch portion 27.

Since the movable stopper 16 and the branch portion 27 are connected to each other with the spring member 15, the expanding and contracting amount of the spring member 15 can be easily defined, thereby allowing the pusher 10 to advance and retreat with high precision.

The engaging portion 23 is disposed in the pusher 10. Accordingly, even after the puncture needle 7 punctures the biological tissue and the anchors 2 are detained by moving the pusher 10, the suture thread 3 can be engage with the pusher. Therefore, by drawing the puncture needle 7 into the proximal side of the outer sheath 8 along with the pusher 10 in which the outer sheath 8 is in contact with the stopper 5 of the suture tool 6, it is possible to move the stopper 5 toward the anchors 2 side. Thereafter, by disengaging the suture thread 3 from the pusher 10, it is possible to detain the suture tool 6 in the biological tissue. Accordingly, it is possible to continuously perform the detention and the suture of the suture tool 6, without replacing a plurality of treatment tools.

At this time, by introducing the loop 18 of the suture thread 3 into the puncture needle 7 through the introduction hole 7b of the puncture needle 7 and inserting the pusher 10 into the loop 18, it is possible to easily engage the loop 18 with the engaging portion 23.

By advancing or retreating the needle slider 12 relative to the operating portion body 11, it is possible to protrude or retreat the puncture needle 7 relative to the outer sheath 8. By advancing or retreating the pusher operating section 13 relative to the needle slider 12, it is possible to advance or retreat the pusher 10 relative to the puncture needle 7. Here, since the branch section 27 is inclined relative to the operating portion body 11, it is possible to continuously operate the needle slider 12 and the pusher operating portion 13 without changing to hold from one portion to another at the time of operating both portions to advance and retreat.

The outer sheath 8 has a coil shape. As a result, even when the puncture needle 7 is retracted into the outer sheath 8, with the suture thread 3 engaged with the engaging portion 23 and the stopper 5 of the suture thread 3 being pressed by the distal end of the outer sheath 8, it can endure well the compressing force generated in the axis direction of the outer sheath 8.

The proximal sheath 8B is covered by the resin tube 24. As a result, when the puncture needle 7 is extruded from the outer sheath 8, it can endure well the tensile force generated in the outer sheath 8.

As shown in FIG. 41, the restriction member 21 is disposed in the puncture needle 7. As a result, when the pusher 10 is inserted into the puncture needle 7 at the time of assembly, the pusher 10 can be inserted into while coming in contact with the gentle slope portion on the proximal side of the restriction member, thereby making assembly work easy. On the other hand, when the pusher 10 is carelessly moved toward the proximal end side of the puncture needle 7 after the assembly, the engaging portion 23 comes in contact with the steep slope portion of the restriction member 21, thereby restricting further movement of the pusher.

According to the suture tool 6, when the suture thread 3 is sandwiched by the thick plate portions 5b and 5c of the distal end of the pair of bent pieces 5B and 5C of the suture tool 6, the contact area between the pair of bent pieces 5B and 5C and the suture thread 3 can be increased more suitably, thereby reducing the stress generated in the pair of bent pieces 5B and 5C. Accordingly, the stopper 5 can keep a stable fixing force to the biological tissue.

When the suture thread 3 is inserted through the stopper 5, the pair of bent pieces 5B and 5C become inclined relative to the base portion 5A. However, when the stopper 5 is moved relative to the suture thread 3 and is fixed to the biological tissue, the pair of bent pieces 5B and 5C and the base portion 5A become substantially parallel to each other again similarly to the initially processed state. That is, since the pair of bent pieces 5B and 5C is returned to the initially processed state, the force for fixing the suture thread 3 is not loosened while the stopper 5 is moved. As a result, it is possible to satisfactorily suppress movement of the bent pieces 5B and 5C relative to the suture thread 3 while it is detained.

Since the thick plate portions 5b and 5c and the engaging protrusions 5d and 5e are engaged with each other when sandwiching the suture thread 3 by the use of the stopper 5, it is possible to satisfactorily prevent the misalignment between the bent pieces 5B and 5C due to a force having a direction intersecting the center axis C of the pair of bent pieces 5B and 5C.

As shown in FIGS. 44 to 47, the portion of the puncture needle 28 in which the introduction hole 28b is formed may be decentered to form a protruding portion 28A. This uses the space S formed between the puncture needle 28 and the outer sheath 8 because the center axis C3 of the outer sheath 8 and the center axis C4 of the puncture needle 28 are offset when the puncture needle 28 is disposed in the outer sheath 8.

Figure 48:
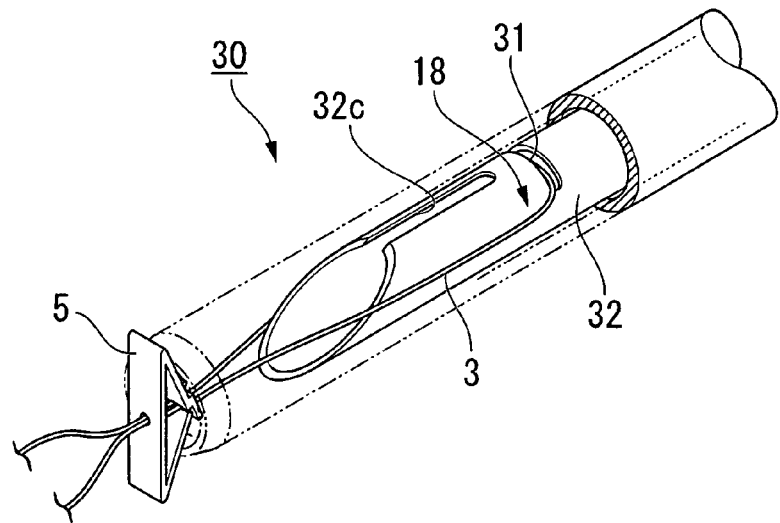
FIG. 48 is a partially enlarged perspective view illustrating a modified example of the suture instrument.

As shown in FIG. 48, an engaging portion 31 of a suture instrument 30 may be disposed in a slit shape on the side surface of a puncture needle 32.

The suture instrument 30 houses the first anchor 2A and the second anchor 2B of the suture tool 6 in series in the puncture needle 32, protrudes the suture thread 3 from a slit 32c, and engages the loop 18 with the engaging portion 31, whereby the stopper 5 is housed in the the outer sheath 8.

Figure 49:
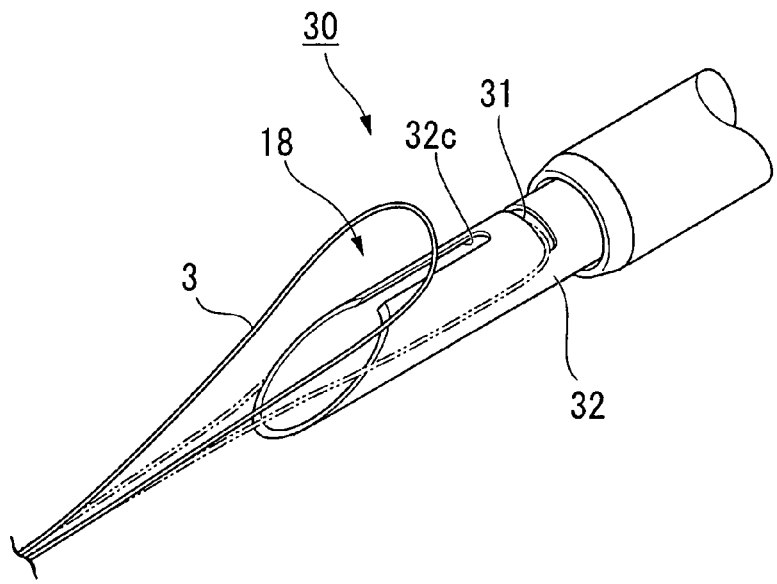
FIG. 49 is an explanatory diagram illustrating an operation of the suture instrument shown in FIG. 48.

By means of the same operation as the first embodiment, an anchor (not shown) of the suture tool 6 is detained. When the suture thread 3 is detached from the engaging portion 31, the puncture needle 32 is protruded from the outer sheath 8 once and then the puncture needle 32 is shaken. At this time, the suture thread 3 is disengaged from the engaging portion 31, as shown in FIG. 49.

According to the suture instrument 30, since the engaging portion 31 has a slit shape, it is possible to easily engage the loop 18 with the surface of the puncture needle 32 by hooking a part of the suture thread 3 thereto.

Figure 50:
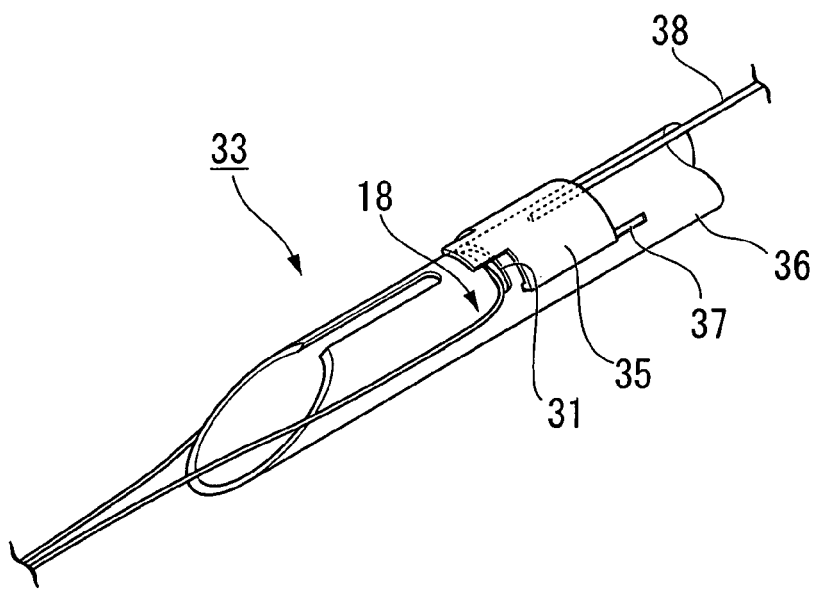
FIG. 50 is a partially enlarged perspective view illustrating a modified example of the suture instrument.

As shown in FIG. 50, a suture instrument 33 may include a cover 35 covering the engaging portion 31. The cover 35 engages with a guide groove 37 formed in the surface of a puncture needle 36 and is connected to a tow member 38 so as to move along the guide groove 37.

According to the suture instrument 33, it is possible to satisfactorily prevent the suture thread 3 from erroneously departing from the engaging portion 31, by covering the engaging portion with the cover 35 after engaging the loop 18 with the engaging portion 31. By towing the towing member 38 to move the cover 35, it is possible to easily disengage the loop 18 from the engaging portion 31.

Figure 51:
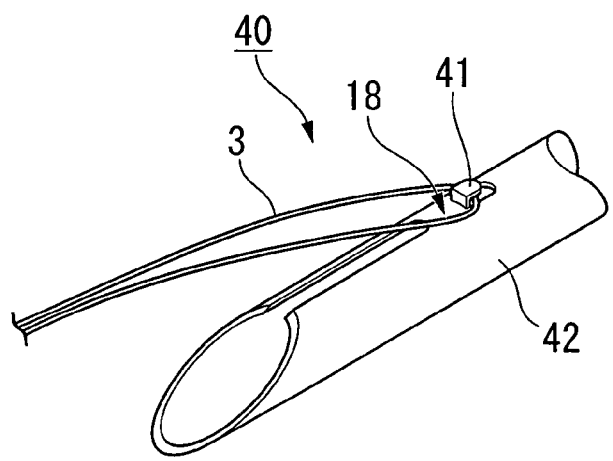
FIG. 51 is a partially enlarged perspective view illustrating a modified example of the suture instrument.

As shown in FIG. 51, an engaging portion 41 of a suture instrument 40 may be disposed to protrude from the side surface of a puncture needle 42.

The suture instrument 40 engages the loop 18 with the engaging portion 41 and detains an anchor which is not shown. When the suture thread 3 is disengaged from the engaging portion 41, the suture thread 3 is disengaged from the engaging portion 41 by protruding the puncture needle 42 once from the outer sheath 8 and shaking the puncture needle 42.

According to the suture instrument 40, since the engaging portion 41 is disposed to protrude, it is possible to easily engage the loop 18 of the suture thread 3 with the surface of the puncture needle 42.

Figure 52:
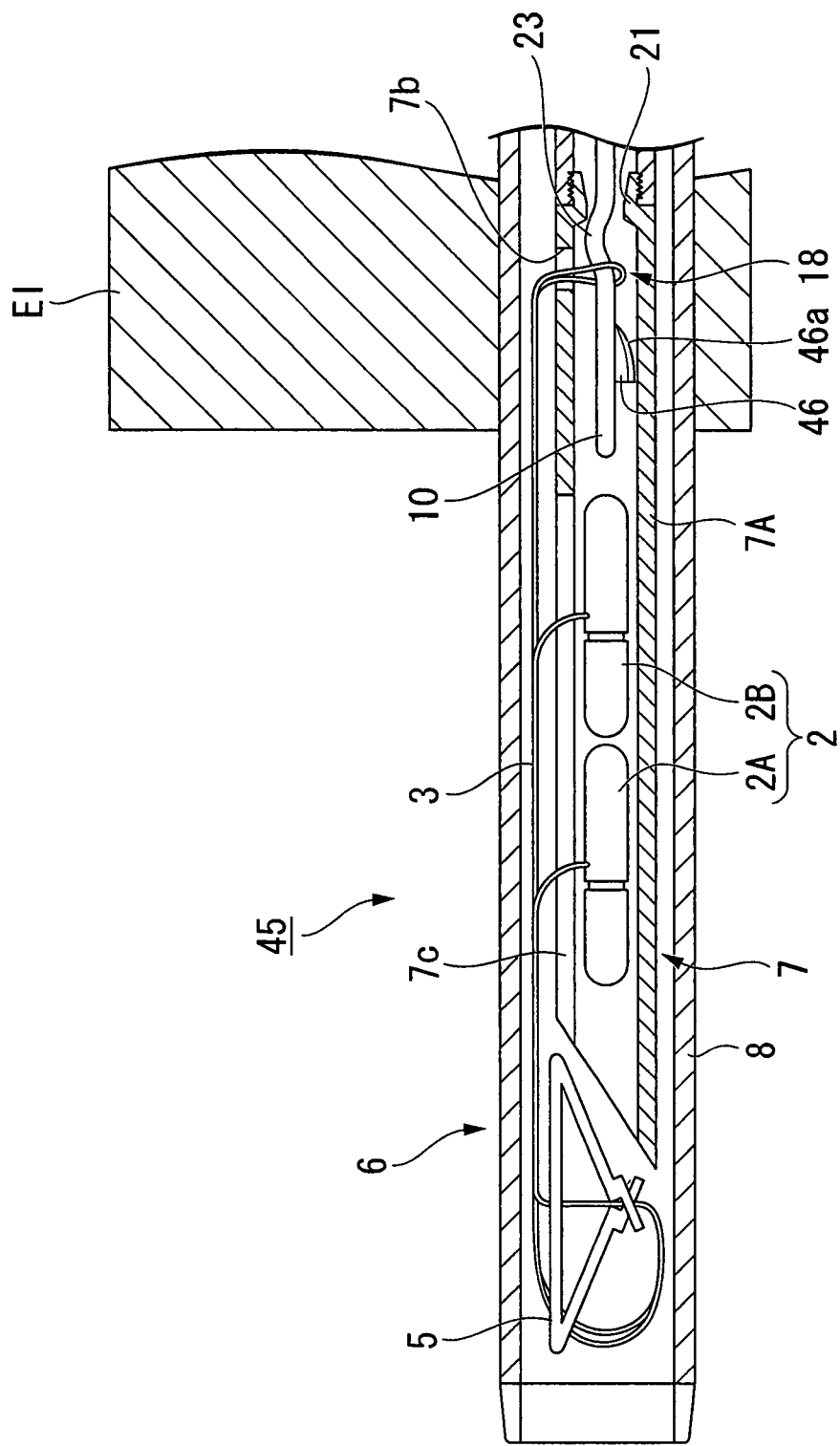
FIG. 52 is a partially enlarged sectional view illustrating a modified example of the suture instrument.

As shown in FIG. 52, the pusher 10 may be provided with a cutting edge 46 which can cut the suture thread 3 of a suture instrument 45.

Here, the cutting edge 46 is disposed closer to the distal end side of the pusher 10 than the engaging portion 23 by a shorter distance than the distance between the introduction hole 7b and the restriction member 21. A cutting edge face 46a is disposed only toward the proximal side.

In the suture instrument 45, by means of the same operation as the first embodiment, the first anchor 2A and the second anchor 2B of the suture tool 6 are housed in series in the puncture needle 7, the suture thread 3 is protruded form the slit 7c, and the loop 18 is introduced into the puncture needle 7 through the introduction hole 7b and is inserted into the distal end of the stopper 5, thereby engage the loop 18 with the engaging portion 23. Here, since the cutting edge face 46a is disposed toward the proximal side, the loop 18 is not cut by the cutting edge 46 while the loop 18 is engaged with the engaging portion.

When the suture thread 3 is disengaged from the engaging portion 23, the pusher 10 is drawn into the proximal side relative to the puncture needle 7. At this time, since the loop 18 comes in contact with the cutting edge face 46a, the loop 18 is cut and the suture thread 3 is disengaged from the engaging portion 23.

According to the suture instrument 45, by relatively moving the pusher 10 in a direction different from the direction in which the loop 18 of the suture thread 3 is inserted, it is possible to easily cut the loop 18 with the cutting edge 46 and to disengage the engagement.

Figure 53:
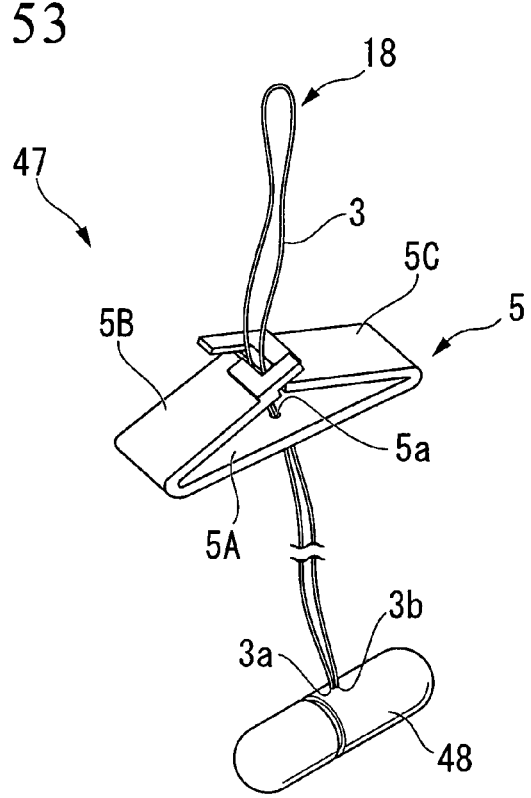
FIG. 53 is a perspective view illustrating an over view of modified example of the suture instrument.

As shown in FIG. 53, when a suture tool 47 has only one anchor 48, a first end 3a and a second end 3b of the suture thread 3 may be connected to the same position of the anchor 48.

Figure 54:
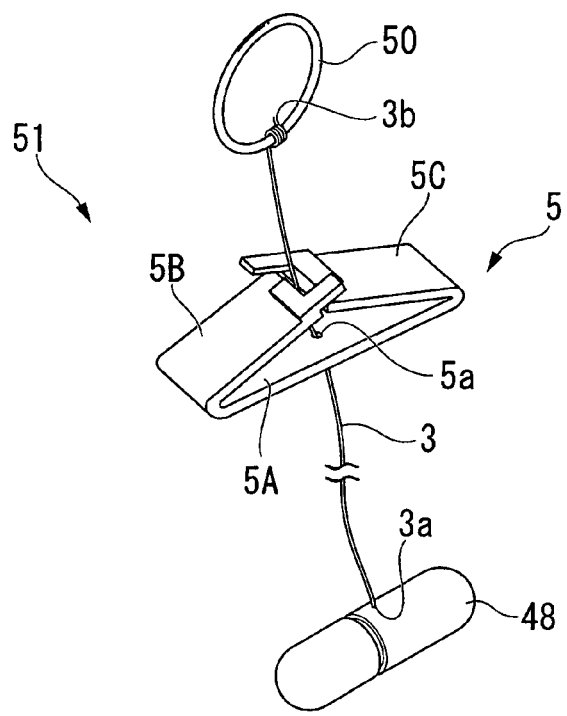
FIG. 54 is a perspective view illustrating an over view of modified example of the suture instrument.

As shown in FIG. 54, a suture tool 51 in which the first end 3a of the suture thread 3 is connected to the anchor 48 and a ring 50 instead of the loop 18 is disposed at the second end 3b may be used.

Figure 55:
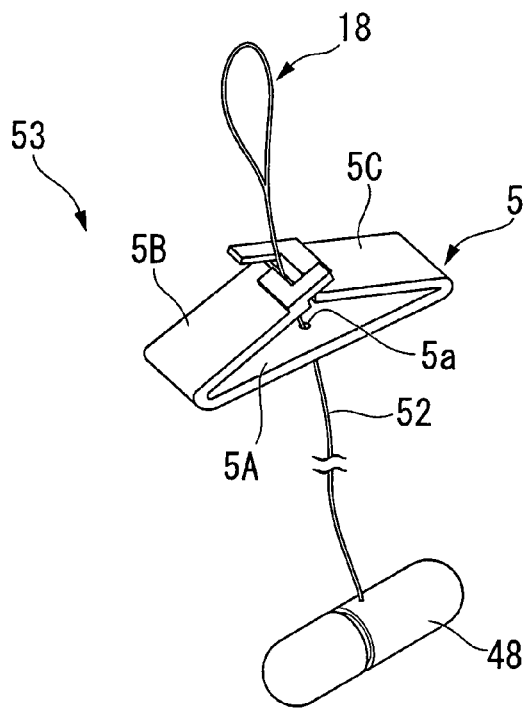
FIG. 55 is a perspective view illustrating an over view of modified example of the suture instrument.
Figure 56:
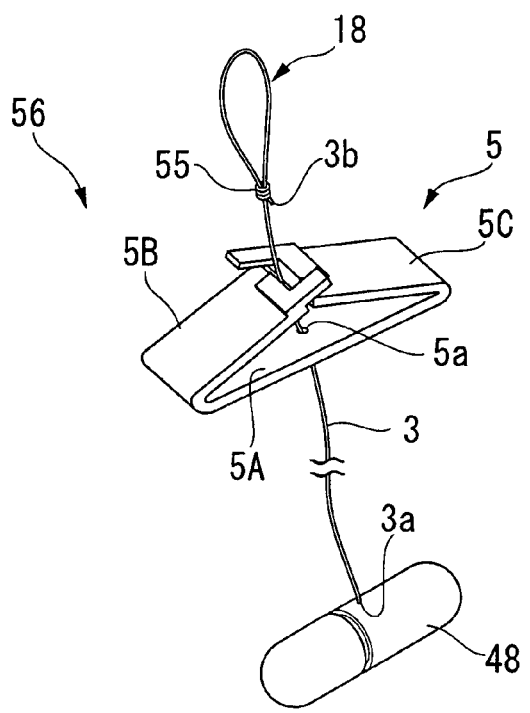
FIG. 56 is a perspective view illustrating an over view of modified example of the suture instrument.
Figure 57:
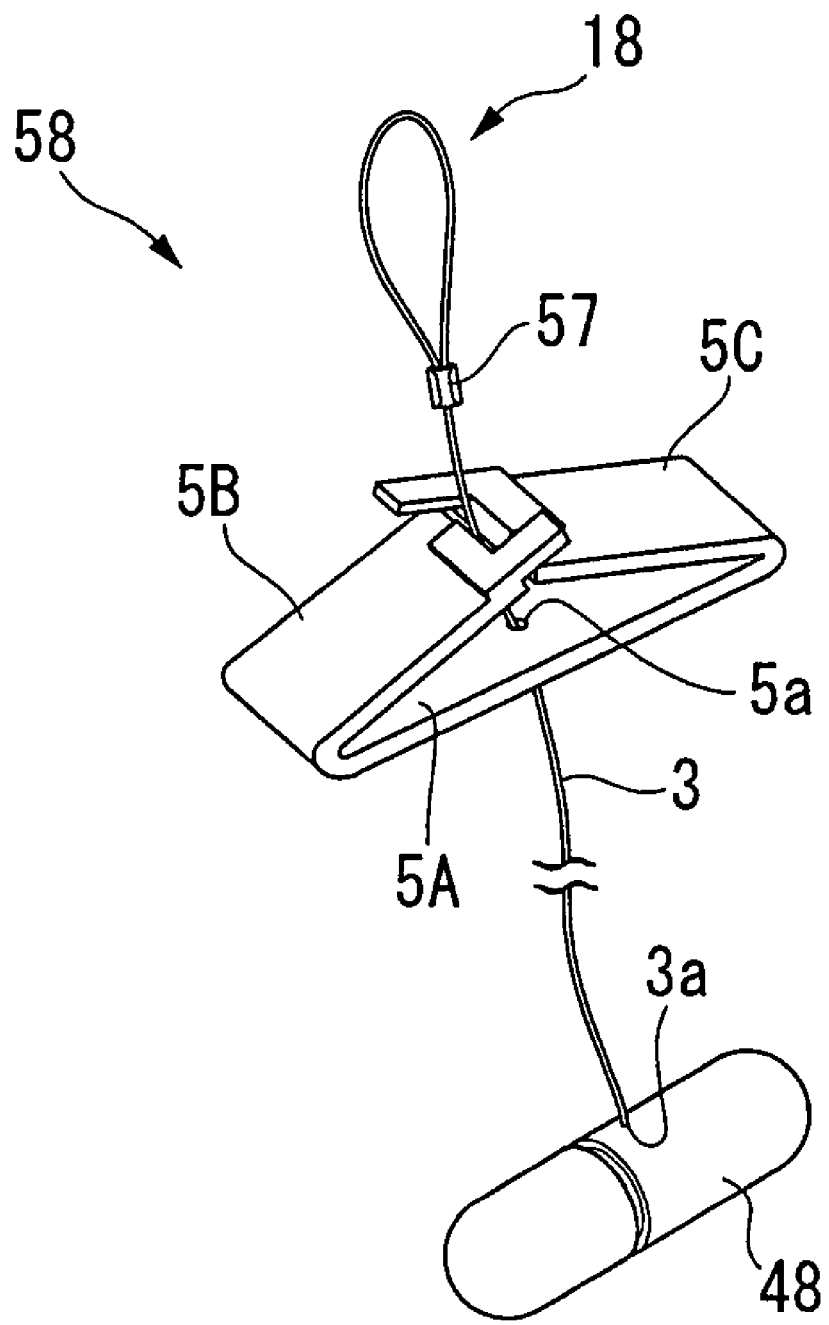
FIG. 57 is a perspective view illustrating an over view of modified example of the suture instrument.

As shown in FIG. 55, a suture tool 53 in which a second end of a suture thread 52 is shaped in advance in a loop 18 may be used. As shown in FIG. 56, a suture tool 56 in which the loop 18 is formed by bending back the suture thread 3 and tying the second end 3b to an intermediate portion of the suture thread 3 to form a knot 55 may be used. Alternatively, as shown in FIG. 57, a suture tool 58 in which the loop 18 is formed by caulking the suture thread with a caulking member 57 may be used.

Second Embodiment

Next, a second embodiment of the invention will be described with reference to FIGS. 58 to 63.

The same elements as the first embodiment are denoted by the same reference numerals and description thereof is omitted.

The second embodiment is different from the first embodiment, in that the endoscopic treatment instrument is a pair of Biopsy test forceps 60 instead of the suture instrument 1.

Figure 58:
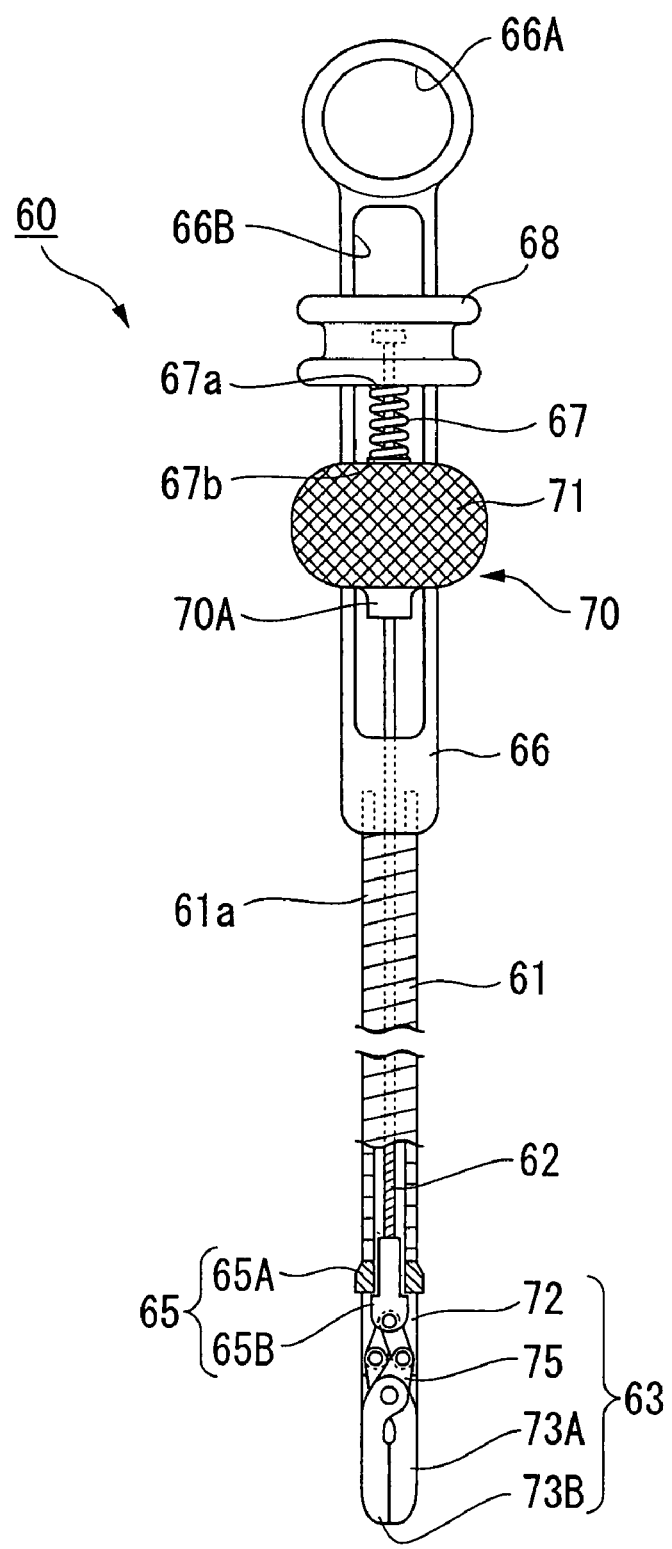
FIG. 58 is a diagram illustrating the entire general appearance of a Biopsy forceps according to a second embodiment of the invention.
Figure 59:
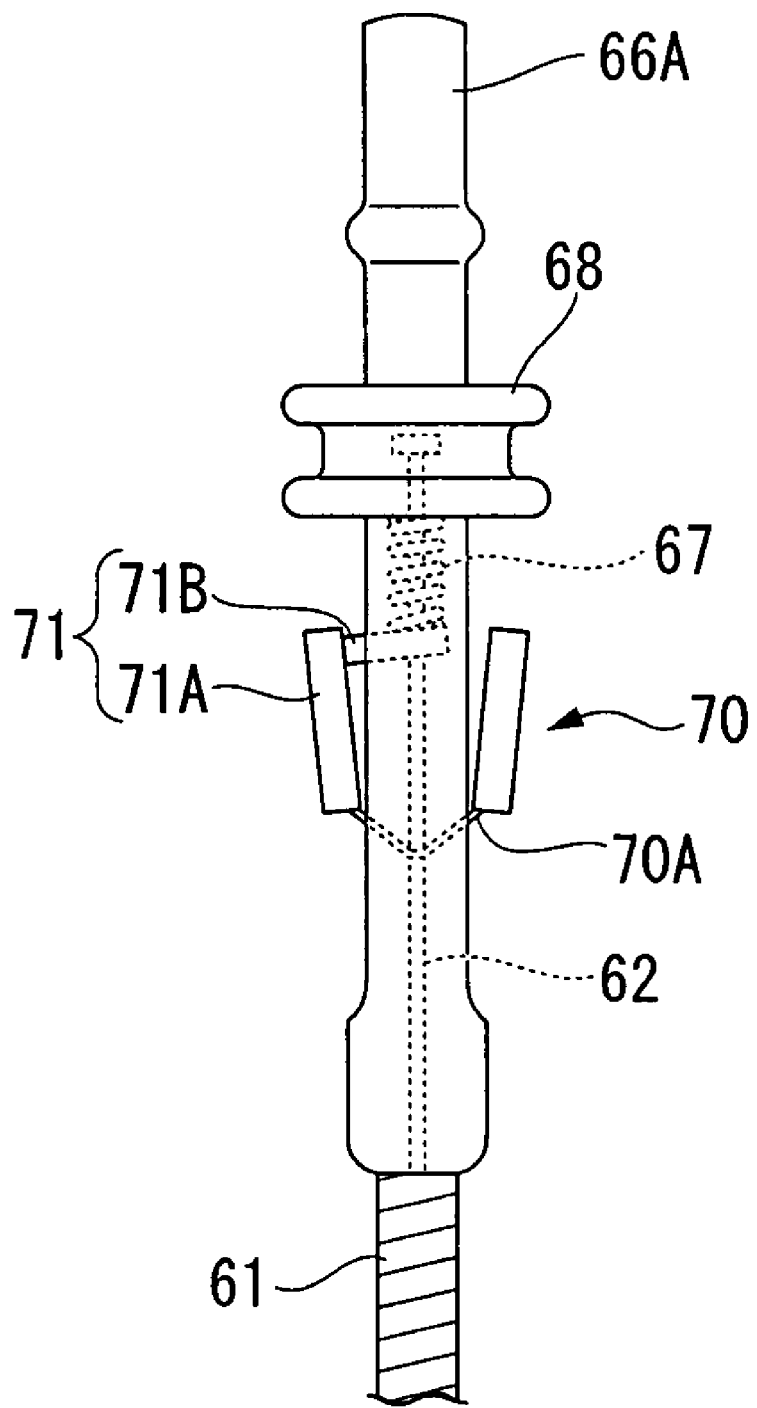
FIG. 59 is a side view illustrating the Biopsy forceps shown in FIG. 58.

As shown in FIGS. 58 to 59, the Biopsy forceps 60 include a flexible sheath 61, an operating wire (wire) 62 which is disposed in the sheath 61 to advance and retreat, a forceps portion 63 connected to distal ends of the sheath 61 and the operating wire 62, a restriction member 65 which restricts the movement of the operating wire 62 in the sheath 61 toward the proximal side, an operating portion 66 connected to the proximal end of the sheath 61, a spring member 67 similar to that of the first embodiment, a slider portion (wire operating portion) 68 connected to the proximal end of the operating wire 62 to advance and retreat relative to the operating portion 66 and connected to a first end 67a of the spring member 67, a movable stopper 70 connected to a second end 67b of the spring member 67 to be movable relative to the operating section 66, and a lock member 71 disposed in the movable stopper 70.

The sheath 61 is constructed by densely winding a metal wire 61a in a coil shape.

The restriction member 65 includes a first restriction member 65A which is formed in a cylindrical shape with substantially the same inner diameter as the inner diameter of the sheath 61 and is disposed at a distal end of the sheath 61 and a second restriction member 65B which is disposed at a distal end of the operating wire 62 and which is formed to protrude outwardly in the diameter direction more than the inner diameter of the sheath 61 and which is formed to be able to come in contact with the first restriction member 65A.

The resilient force of the spring member 67 is controlled to be smaller than the frictional force between the operating wire 62 and the sheath 61.

The forceps portion 63 includes a front cover 72 disposed at the distal end of the sheath 61, a pair of forceps pieces 73A and 73B, and a link portion 75 which is connected to the distal end of the second restriction member 65B and which converts an advancing and retreating operation of the operating wire 62 into an opening and closing operation of the pair of forceps pieces 73A and 73B.

The operating portion 66 extends from the proximal end of the sheath 61 and a finger laying portion 66A is disposed at the proximal end thereof. The operating portion 66 is provided with a slit 66B which extends in the longitudinal direction and which is wide enough so that the operating wire 62 is inserted therethrough.

The slider portion 68 is disposed to be slidable in the longitudinal direction in a state where it engages with the slit 66B of the operating portion 66.

The movable stopper 70 includes a connection portion 70A connected to the operating wire 62 and the lock member 71 is connected to the proximal end side of the connection portion 70A.

The lock member 71 includes a contact portion 71A pressed onto the outer circumferential surface of the operating section 66 and a connection portion 71B which extends into the slit 66B of the operating portion 66, into which the operating wire 62 is inserted to advance and retreat, and which is connected to the second end 67b of the spring member 67. The contact portion 71A has a size which can be pressed by a finger.

Next, an operation of the Biopsy forceps 60 according to this embodiment will be described with reference to FIGS. 60 to 63. The Biopsy forceps 60 are inserted into an endoscope insertion section of an endoscope (not shown) inserted into a living body.

Figure 60:
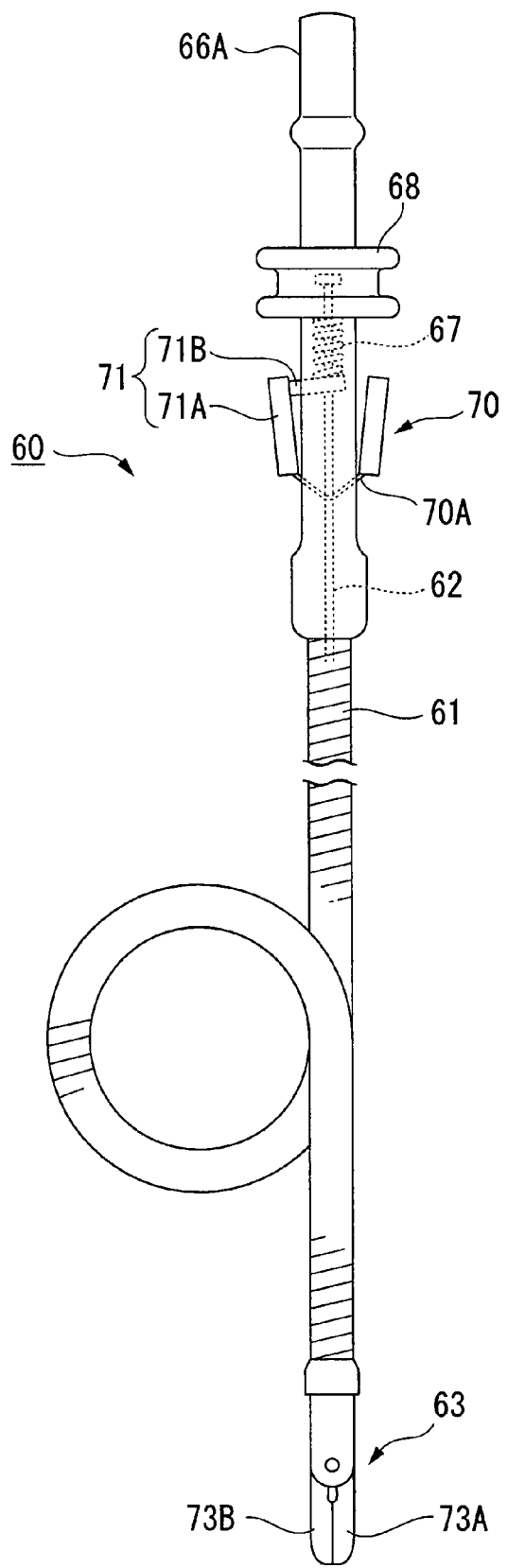
FIG. 60 is an explanatory diagram illustrating an operation of the Biopsy forceps.

Depending on the use states, the sheath 61 can be changed to the curved state as shown in FIG. 60 from the straightly expanded state as shown in FIGS. 58 and 59, in order to define the biological test direction.

At this time, since the proximal side portion of the sheath 61 is soft, the sheath 61 is expanded in a curved direction. On the other hand, the operating wire 62 does not expand and contract. Accordingly, the second restriction member 65B disposed in the operating wire 62 is locked to the first restriction member 65A disposed in the sheath 61 and thus the slider portion 68 is drawn into the distal end side of the operating portion 66 along with the movable stopper 70.

Figure 61:
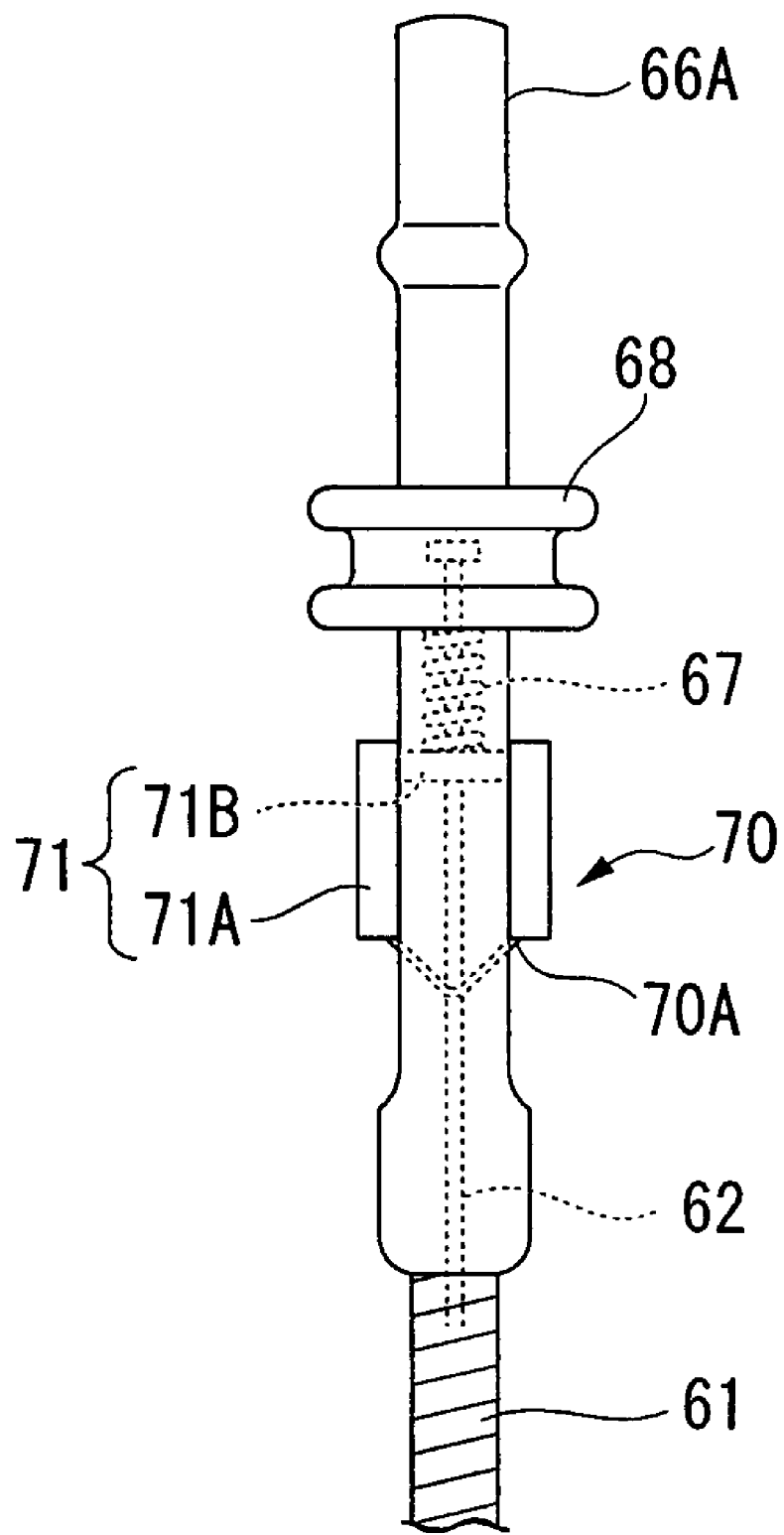
FIG. 61 is an explanatory diagram illustrating an operation of the Biopsy forceps.
Figure 62:
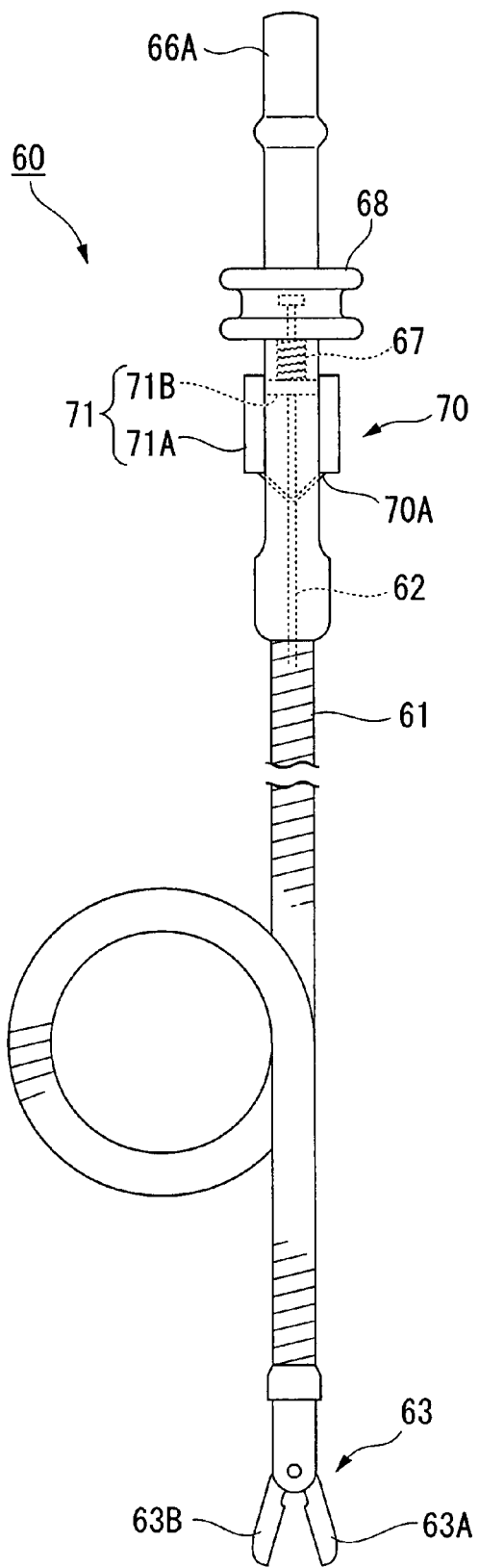
FIG. 62 is an explanatory diagram illustrating an operation of the Biopsy forceps.

Next, as shown in FIG. 61, the lock member 71 of the movable stopper 70 is grasped to bring the contact portion 71A into contact with the operating portion 66. As shown in FIG. 62, the slider portion 68 is moved relative to the operating portion 66 to compress the spring member 67. At this time, the operating wire 62 is moved by a predetermined length relative to the sheath 61 and thus the pair of forceps pieces 73A and 73B is opened by half.

Subsequently, the lock member 71 is released and restored to the original state. Here, the resilient force of the spring member 67 is smaller than the frictional force between the operating wire 62 and the sheath 61. Accordingly, while the spring member 67 is restored to the original state without the relative movement between the operating wire 62 and the sheath 61, the movable stopper 70 advances relative to the operating portion 66.

Figure 63:
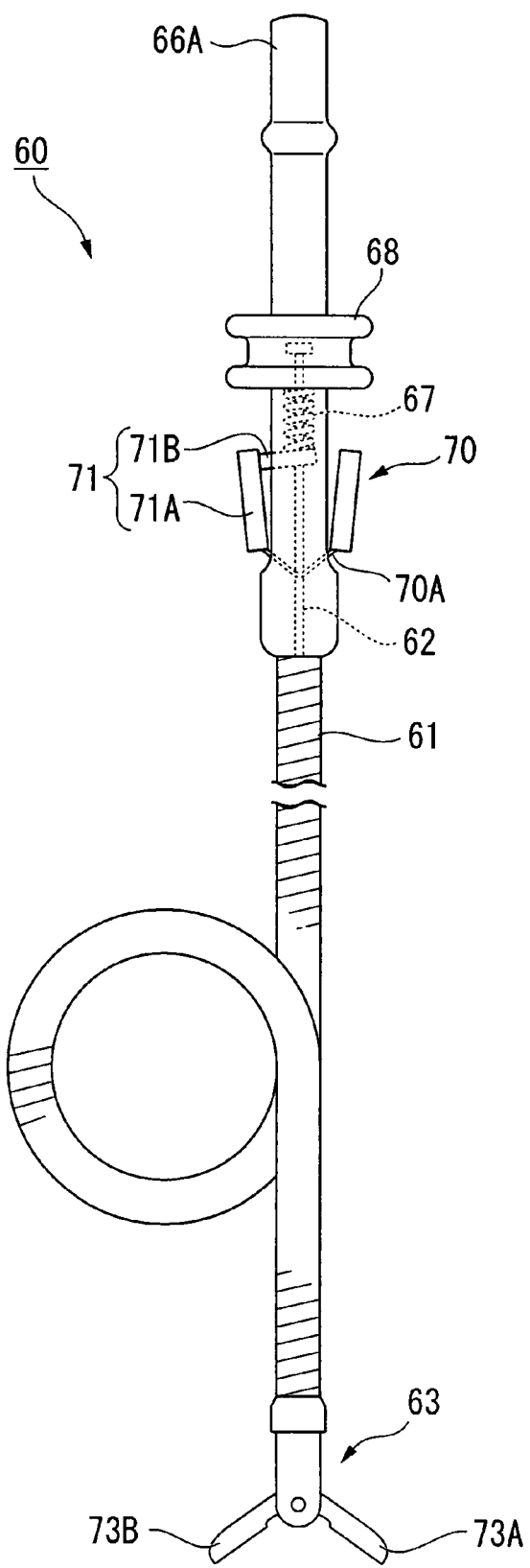
FIG. 63 is an explanatory diagram illustrating an operation of the Biopsy forceps.

Here, when the pair of forceps pieces 73A and 73B is closed, the slider portion 68 is moved toward the proximal side relative to the operating portion 66. On the other hand, as shown in FIG. 63, when the pair of forceps pieces 73A and 73B is further opened to the maximum position, the slider portion 68 is further advanced relative to the operating portion 66.

According to the Biopsy forceps 60, even when the movable stopper 70 is set to the movable state and the spring member is set to the expanding state so as to curve the sheath 61, it is possible to prevent the pair of forceps pieces 73A and 73B from being opened or closed, by moving the operating wire 62 relative to the operating portion 66 in accordance with the expansion and contraction of the sheath 61. In addition, by moving the operating wire 62 relative to the sheath 61 by a predetermined distance in a state where the movable stopper 70 is set to the fixed state and the spring member 67 is set to the contracted state by the use of the lock member 71, it is possible to open or close the pair of forceps pieces 73A and 73B by a predetermined amount.

Although exemplary embodiments of the invention have been described hitherto, the invention is not limited to the exemplary embodiments. The elements of the invention may be added, omitted, or replaced without departing from the gist of the invention. The invention is not restricted by only the above description, but by only the scope of the appended claims.

What is claimed is:

1. An endoscopic treatment instrument comprising:
a flexible sheath;
a wire disposed inside the sheath so as to advance and retreat;
a restriction member which restricts movement of the wire in the sheath to a proximal side;
an operating portion connected to a proximal end of the sheath;
a wire operating portion which is connected to a proximal end of the wire and disposed to advance and retreat relative to the operating portion;
a resilient member which has a first end and a second end, wherein the first end is connected to the wire operating portion and wherein the first end of the resilient member expands and contracts from the second end;
a movable member which is connected to the second end so as to be movable relative to the operating portion; and
a control member which is disposed in the movable member and which switches the movable member between a movable state and a fixed state relative to the operating portion,
wherein the sheath further comprises:
a hollow puncture needle which houses the wire having a hard needle portion disposed at the distal end thereof so as to advance and retreat; and
an outer sheath which houses the puncture needle so as to advance and retreat, wherein a resilient restoring force of the resilient member is set to be smaller than a frictional force generated over an entire length between the wire and the puncture needle.

2. The endoscopic treatment instrument according to claim 1, wherein the movable member is slidable relative to the operating portion, and wherein the control member protrudes from the movable member and is resiliently deformed in a direction of reducing a diameter of the movable member.

3. The endoscopic treatment instrument according to claim 1, wherein the resilient member is a spring member.

* * * * *